United States Patent
Levine

(10) Patent No.: US 9,833,621 B2
(45) Date of Patent: Dec. 5, 2017

(54) MODULATION OF SIRTUINS BY VAGUS NERVE STIMULATION

(75) Inventor: Jacob A. Levine, Queens, NY (US)

(73) Assignee: SETPOINT MEDICAL CORPORATION, Valencia, CA (US)

( * ) Notice: Subject to any disclaimer, the term of this patent is extended or adjusted under 35 U.S.C. 154(b) by 0 days.

(21) Appl. No.: 13/338,185

(22) Filed: Dec. 27, 2011

(65) Prior Publication Data

US 2013/0079834 A1 Mar. 28, 2013

Related U.S. Application Data

(60) Provisional application No. 61/538,580, filed on Sep. 23, 2011.

(51) Int. Cl.
*A61N 1/00* (2006.01)
*A61N 1/36* (2006.01)
*A61K 9/00* (2006.01)

(52) U.S. Cl.
CPC ........ *A61N 1/36053* (2013.01); *A61K 9/0009* (2013.01); *A61N 1/36146* (2013.01)

(58) Field of Classification Search
CPC ............ A61N 1/36053; A61N 1/36146; A61K 9/0009
USPC ................................. 607/45, 46, 3
See application file for complete search history.

(56) References Cited

U.S. PATENT DOCUMENTS

| | | |
|---|---|---|
| 2,164,121 A | 6/1939 | Pescador |
| 3,363,623 A | 1/1968 | Atwell |
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |

(Continued)

FOREIGN PATENT DOCUMENTS

| | | |
|---|---|---|
| CN | 201230913 | 5/2009 |
| CN | 101528303 A | 9/2009 |

(Continued)

OTHER PUBLICATIONS

US 6,184,239, 02/2001, Puskas (withdrawn)

(Continued)

*Primary Examiner* — Mallika D Fairchild
(74) *Attorney, Agent, or Firm* — Shay Glenn LLP

(57) ABSTRACT

Systems, devices and methods for modulation of sirtuins by neurostimulation. In particular, sirtuins may be modulated by stimulation of the vagus nerve. Further described herein generally are methods, systems and devices, for specifically modulating sirtuins, including sub-sets (types or localized regions) of sirtuins by vagus nerve stimulation (VNS).

24 Claims, 19 Drawing Sheets

(56) References Cited

U.S. PATENT DOCUMENTS

| | | |
|---|---|---|
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thomspon et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |

(56) References Cited

U.S. PATENT DOCUMENTS

| | | |
|---|---|---|
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 * | 3/2008 | Nunes et al. ................ 548/154 |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,577,458 B1 | 11/2013 | Libbus et al. |
| 8,600,505 B2 | 12/2013 | Libbus et al. |
| 8,630,709 B2 | 1/2014 | Libbus et al. |
| 8,843,210 B2 | 9/2014 | Simon et al. |
| 8,918,178 B2 | 12/2014 | Simon et al. |
| 8,918,191 B2 | 12/2014 | Libbus et al. |
| 8,983,628 B2 | 3/2015 | Simon et al. |
| 8,983,629 B2 | 3/2015 | Simon et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,410 B2 | 12/2015 | Levine et al. |
| 9,254,383 B2 | 2/2016 | Simon et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,662,490 B2 | 5/2017 | Tracey et al. |
| 9,700,716 B2 | 7/2017 | Faltys et al. |
| 2001/0002441 A1 | 5/2001 | Boveja |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |

(56) References Cited

U.S. PATENT DOCUMENTS

| | | |
|---|---|---|
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0125044 A1 | 6/2005 | Tracey et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0282906 A1 | 12/2005 | Tracey et al. |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |

(56) References Cited

U.S. PATENT DOCUMENTS

| | | |
|---|---|---|
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0234790 A1 | 9/2008 | Bayer et al. |
| 2008/0249439 A1 | 10/2008 | Tracey et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0062874 A1 | 3/2009 | Tracey et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0247934 A1 | 10/2009 | Tracey et al. |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2010/0003656 A1 | 1/2010 | Kilgard et al. |
| 2010/0010581 A1 | 1/2010 | Goetz et al. |
| 2010/0010603 A1 | 1/2010 | Ben-David et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0125304 A1 | 5/2010 | Faltys |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0249859 A1 | 9/2010 | DiLorenzo |
| 2010/0280569 A1 | 11/2010 | Bobillier et al. |
| 2010/0312320 A1 | 12/2010 | Faltys et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0106208 A1 | 5/2011 | Faltys et al. |
| 2011/0144717 A1 | 6/2011 | Burton et al. |
| 2011/0190849 A1 | 8/2011 | Faltys et al. |
| 2011/0224749 A1 | 9/2011 | Ben-David et al. |
| 2011/0307027 A1 | 12/2011 | Sharma et al. |
| 2012/0065706 A1 | 3/2012 | Vallapureddy et al. |
| 2012/0185009 A1 | 7/2012 | Kornet et al. |
| 2012/0185020 A1 | 7/2012 | Simon et al. |
| 2013/0066392 A1 | 3/2013 | Simon et al. |
| 2013/0066395 A1 | 3/2013 | Simon et al. |
| 2013/0317580 A1 | 11/2013 | Simon et al. |
| 2015/0100100 A1 | 4/2015 | Tracey et al. |
| 2015/0241447 A1 | 8/2015 | Zitnik et al. |
| 2016/0038745 A1 | 2/2016 | Faltys et al. |
| 2016/0067497 A1 | 3/2016 | Levine et al. |
| 2016/0096017 A1 | 4/2016 | Levine et al. |
| 2016/0114165 A1 | 4/2016 | Levine et al. |
| 2016/0331952 A1 | 11/2016 | Faltys et al. |
| 2016/0367808 A9 | 12/2016 | Simon et al. |
| 2017/0113044 A1 | 4/2017 | Levine et al. |

FOREIGN PATENT DOCUMENTS

| | | |
|---|---|---|
| CN | 101578067 A | 11/2009 |
| CN | 101868280 A | 10/2010 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 0/1910 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |

OTHER PUBLICATIONS

Levine et al.; U.S. Appl. No. 13/467,928 entitled "Single-Pulse Activation of the Cholinergic Anti-Inflammatory Pathway to Treat Chronic Inflammation," filed May 9, 2012.

Levine et al.; U.S. Appl. No. 13/851,013 entitled "Devices and methods for modulation of bone erosion," filed Mar. 26, 2013.

Tracey, K. J.; Reflex control of immunity; Nat Rev Immunol; 9(6); pp. 418-428; Jun. 2009.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); pp. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

(56) References Cited

OTHER PUBLICATIONS

Bernik et al., Vagus nerve stimulation attenuates cardiac TNF production in endotoxic shock, (supplemental to SHOCK, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression IN shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to SHOCK, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to SHOCK, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, pp. 189-204, (month unavailable) 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cicala et al., "Linkage between inflammation and coagulation: An update on the molecular basis of the crosstalk," Life Sciences, vol. 62(20); pp. 1817-1824, Apr. 1998.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
Das, Critical advances in spticemia and septic shock, Critical Care, vol. 4, pp. 290-296, Sep. 7, 2000.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Doshi et al., Evolving role of tissue factor and its pathway inhibitor, Crit. Care Med., vol. 30, suppl. 5, pp. S241-S250, May 2002.
Ellington et al., In vitro selection of RNA molecules that bind specific ligands, Nature, vol. 346, pp. 818-822, Aug. 30, 1990.
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(-)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, SHOCK, vol. 27, No. 4, pp. 443-447, Apr. 2007.

(56) References Cited

OTHER PUBLICATIONS

Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; (month unavailable) 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby—Year Book, inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Neural regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (month unavailable) 2001.
Katagiri, M., et al., Increased cytokine production by gastric mucosa in patients with helicobacter pylori infection, J. Clin, Gastroenterol., vol. 25, Suppl. 1, pp. S211-S214, (month unavailable) 1997.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Krarup et al; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, SHOCK, vol. 5, No. 5, pp. 385-388, May 1996.
Kuznik, "Role of the vascular wall in the process of hemostatis," Usp Sovrem Biol., vol. 75(1): pp. 61-85, (month unavailable) 1973.
Kuznik, et al., "Blood Coagulation in stimulation of the vagus nerve in cats," Biull. Eskp. Biol. Med., vol. 78(7): pp. 7-9, (month unavailable) 1974.
Kuznik, et al., "Heart as an efferent regulator of the process of blood coagulation and fibrinolysis," Kardiologiia, vol. 13(3): pp. 10-17, (month unavailable) 1973.
Kuznik, et al., "Role of the heart and vessels in regulating blood coagulation and fibrinolysis," Kagdiologiia, vol. 13(4): pp. 145-154, (month unavailable) 1973.
Kuznik, et al., "Secretion of blood coagulation factors into saliva under conditions of hypo-and hypercoagulation," Voprosy Meditsinskoi Khimii, vol. 19(1): pp. 54-57; (month unavailable) 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (month unavailable) 1975.

(56) References Cited

OTHER PUBLICATIONS

Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; (month unavailable) 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Martindale: The Extra Pharmacopoeia; 28th Ed. London; The pharmaceutical press; pp. 446-485; (month unavailable) 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, (month unavailable) 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; (month unavailable) 2004.
Mishchenko, et al., "Coagulation of the blood and fibrinolysos in dogs during vagal stimulation," Sechenov Physiological Journal of the USSR, vol. 61(1): pp. 101-107, (month unavailable) 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, (month unavailable) 1974.
Molina et al., CNI-1493 attenuates hemodynamic and pro-inflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al.,"Treatment of Botkin's disease with heparin," Klin. Med., vol. 51(3): pp. 113-117, Mar. 1973.
Payne, J. B. et al., Nicotine effects on PGE2 and IL-1 beta release by LPS-treated human monocytes, J. Perio. Res., vol. 31, No. 2, pp. 99-104, Feb. 1996.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Rinner et al.; Rat lymphocytes produce and secrete acetylcholine in dependence of differentiation and activation; J.Neuroimmunol.; 81(1-2); pp. 31-37; Jan. 1998.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, (month unavailable) 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.

(56) References Cited

OTHER PUBLICATIONS

Sokratov, et al. "The role of choline and adrenegic structures in regulation of renal excretion of hemocoagulating compounds into the urine," Sechenov Physiological Journal of the USSR, vol. 63(12): pp. 1728-1732, (month unavailable) 1977.

Stalcup et al., Endothelial cell functions in the hemodynamic responses to stress, Annals of the New York Academy of Sciences, vol. 401, pp. 117-131, Dec. 1982.

Steinlein, New functions for nicotine acetylcholine receptors?, Behavioural Brain Res., vol. 95, pp. 31-35, (month unavailable) 1998.

Sternberg, E. M., Perspectives series: cytokines and the brain 'neural-immune interactions in health and disease,' J. Clin. Invest., vol. 100, No. 22, pp. 2641-2647, Dec. 1997.

Strojnik et al.; Treatment of drop foot using and implantable peroneal underknee stimulator; Scand. J. Rehab. Med.; vol. 19(1); pp. 37R43; (month unavailable) 1987.

Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.

Suter et al.; Do glial cells control pain?; Neuron Glia Biol.; vol. 3; No. 3; pp. 255-268; Aug. 2007.

Sykes, et al., An investigation into the effect and mechanisms of action of nicotine in inflammatory bowel disease, Inflamm. Res., vol. 49, pp. 311-319, Jul. 2000.

Takeuchi et al., A comparision between chinese blended medicine "Shoseiryuto" tranilast and ketotifen on the anit-allergic action in the guinea pigs, Allergy, vol. 34, No. 6, pp. 387-393, Jun. 1985 (eng. abstract).

Toyabe, et al., Identification of nicotinic acetylcholine receptors on lymphocytes in the periphery as well as thymus in mice, Immunology, vol. 92(2), pp. 201-205, Oct. 1997.

Tracey et al., Mind over immunity, Faseb Journal, vol. 15, No. 9, pp. 1575-1576, Jul. 2001.

Tracey, K. J. et al., Anti-cachectin/TNF monoclonal antibodies prevent septic shock during lethal bacteraemia; Nature, 330: pp. 662-664, Dec. 23, 1987.

Tracey, K. J. et al., Physiology and immunology of the cholinergic antiinflammatory pathway; J Clin Invest.; vol. 117: No. 2; pp. 289-296; Feb. 2007.

Tracey, K. J. et al., Shock and tissue injury induced by recombinant human cachectin, Science, vol. 234, pp. 470-474, Oct. 24, 1986.

Tracey, K.J., The inflammatory reflex, Nature, vol. 420, pp. 853-859, Dec. 19-26, 2002.

Tsutsui, H., et al., Pathophysiolocical roles of interleukin-18 in inflammatory liver diseases; Immunol. Rev., 174:192-209, Apr. 2000.

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.

Van Der Horst et al.; Stressing the role of FoxO proteins in lifespan and disease; Nat Rev Mol Cell Biol.; vol. 8; No. 6; pp. 440-450; Jun. 2007.

Vanhoutte, et al., Muscarinic and beta-adrenergic prejunctional modulation of adrenergic neurotransmission in the blood vessel wall, Gen Pharmac., vol. 14, pp. 35-37, (month unavailable) 1983.

vanWesterloo, et al., The cholinergic anti-inflammatory pathway regulates the host response during septic peritonitis, The Journal of Infectious Diseases, vol. 191, pp. 2138-2148, Jun. 15, 2005.

Ventureyra, Transcutaneous vagus nerve stimulation for partial onset seizure therapy, Child's Nery Syst, vol. 16(2), pp. 101-102, (month unavailable) 2000.

Vijayaraghavan, S.; Glial-neuronal interactions-implications for plasticity anddrug addictionl AAPS J.; vol. 11; No. 1; pp. 123-132; Mar. 2009.

Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.

Von Känal, et al., Effects of non-specific ?-adrenergic stimulation and blockade on blood coagulation in hypertension, J. Appl. Physiol., vol. 94, pp. 1455-1459, Apr. 2003.

Von Känal, et al., Effects of sympathetic activation by adrenergic infusions on hemostasis in vivo, Eur. J. Haematol., vol. 65: pp. 357-369, Dec. 2000.

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF-? dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-1066; Feb. 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yeh, S.S. et al., Geriatric cachexia: the role of cytokines, Am. J. Clin. Nutr., vol. 70(2), pp. 183-197, Aug. 1999.

Zhang et al., Tumor necrosis factor, The Cytokine Handbook, 3rd ed., Ed. Thompson, Academic Press, pp. 517-548, Jul. 1, 1998.

Zhang et al.; Roles of SIRT1 in the acute and restorative phases following induction of inflammation.; J Biol Chem.; vol. 285; No. 53; pp. 41391-41401; Dec. 2010.

Robinson et al.; Studies with the Electrocardiograph on the Action of the Vagus Nerve on the Human Heart; J Exp Med; 14(3):217-234; Sep. 1911.

Faltys et al.; U.S. Appl. No. 14/082,047 entitled "Neural Stimulation Devices and Systems for Treatment of Chronic Inflammation," filed Nov. 15, 2013.

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.

Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

Cheyuo et al.; The parasympathetic nervous system in the quest for stroke therapeutics; J. Cereb. Blood Flow Metab.; 31(5); pp. 1187-1195; May 2011.

(56) References Cited

OTHER PUBLICATIONS

Clark et al.; Enhanced recognition memory following vagus nerve stimulation in human subjects; Nat. Neurosci.; 2(1); pp. 94-98; Jan. 1999.
Diamond et al.; Mapping the immunological homunculus; Proc. Natl. Acad. Sci. USA; 108(9); pp. 3461-3462; Mar. 1, 2011.
Dorr et al.; Effect of vagus nerve stimulation on serotonergic and noradrenergic transmission; J. Pharmacol. Exp. Ther.; 318(2); pp. 890-898; Aug. 2006.
Ellrich et al.; Transcutaneous vagus nerve stimulation; Eur. Neurological Rev.; 6(4); pp. 254-256; Winter 2011.
Engineer et al.; Reversing pathological neural activity using targeted plasticity; Nature; 470(7332); pp. 101-104; Feb. 3, 2011 (Author Manuscript).
Gao et al.; Investigation of specificity of auricular acupuncture points in regulation of autonomic function in anesthetized rats; Autonomic Neurosc.; 138(1-2); pp. 50-56; Feb. 29, 2008.
Groves et al.; Recordings from the rat locus coeruleus during acute vagal nerve stimulation in the anaesthetised rat; Neuroscience Letters; 379(3); pp. 174-179; May 13, 2005.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Peuker; The nerve supply of the human auricle; Clin. Anat.; 15(1); pp. 35-37; Jan. 2002.

Swick et al.; Locus coeruleus neuronal activity in awake monkeys: relationship to auditory P300-like potentials and spontaneous EEG. Exp. Brain Res.; 101(1); pp. 86-92; Sep. 1994.
Tekdemir et al.; A clinico-anatomic study of the auricular branch of the vagus nerve and arnold's ear-cough reflex; Surg. Radiol. Anat.; 20(4); pp. 253-257; Mar. 1998.
Zamotrinsky et al.; Vagal neurostimulation in patients with coronary artery disease; Auton. Neurosci.; 88(1-2); pp. 109-116; Apr. 2001.
Faltys et al.; U.S. Appl. No. 15/406,619 entitled "Systems and methods for establishing a nerve block," filed Jan. 13, 2017.
Levine et al.; U.S. Appl. No. 15/411,933 entitled "Control of vagal stimulation," filed Jan. 20, 2017.
Zitnik et al.; U.S. Appl. No. 15/411,936 entitled "Implantable microstimulators and inductive charging systems," filed Jan. 20, 2017.
Faltys et al.; U.S. Appl. No. 15/415,764 entitled "Implantable neurostimulator having power control and thermal regulation and methods of use," filed Jan. 25, 2017.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Pavlov et al; Controlling inflammation: the cholinergic anti-inflammatory pathway; Biochem. Soc. Trans.; 34(Pt 6); pp. 1037-1040; Dec. 2006.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Stevens et al.; The anti-inflammatory effect of some immunosuppressive agents; J. Path.; 97(2); pp. 367-373; 1969 (year of pub. sufficiently earlier than effective US filing date and any foreign priority date).

\* cited by examiner

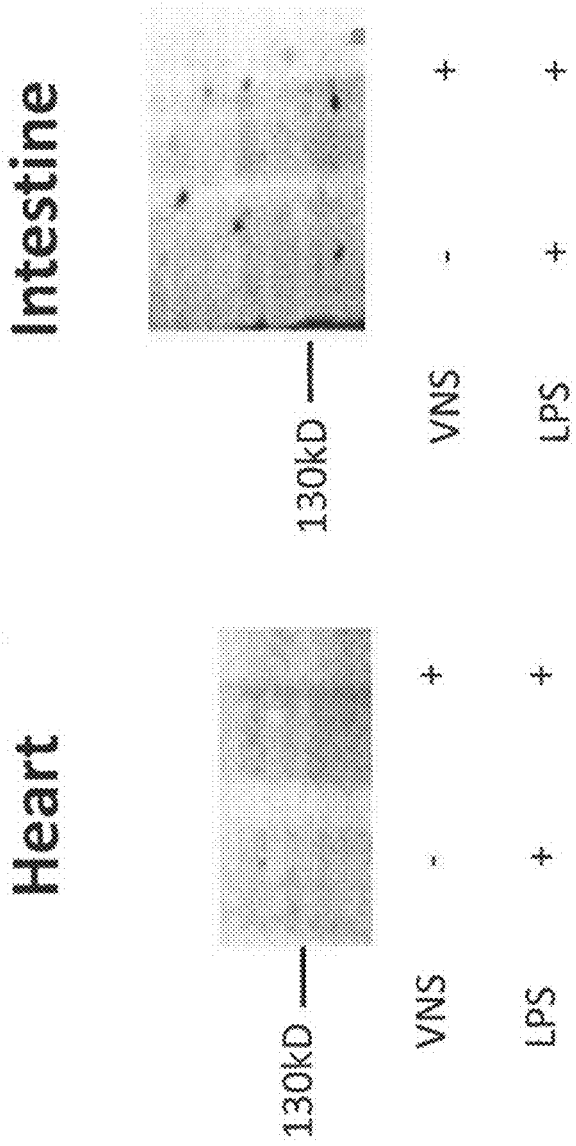

VNS up-regulates or maintains SIRT3 in Intestine (distal jejunum) and fat in Endotoxemia FIG. 5A
Intestine 34kD —

| VNS | - | + |
| LPS | + | + |

FIG. 5B
Fat

| VNS | - | + | + |
| LPS | + | + | + |

35kD —

FIG. 5C
Fat

| VNS | + | - |
| LPS | - | - |

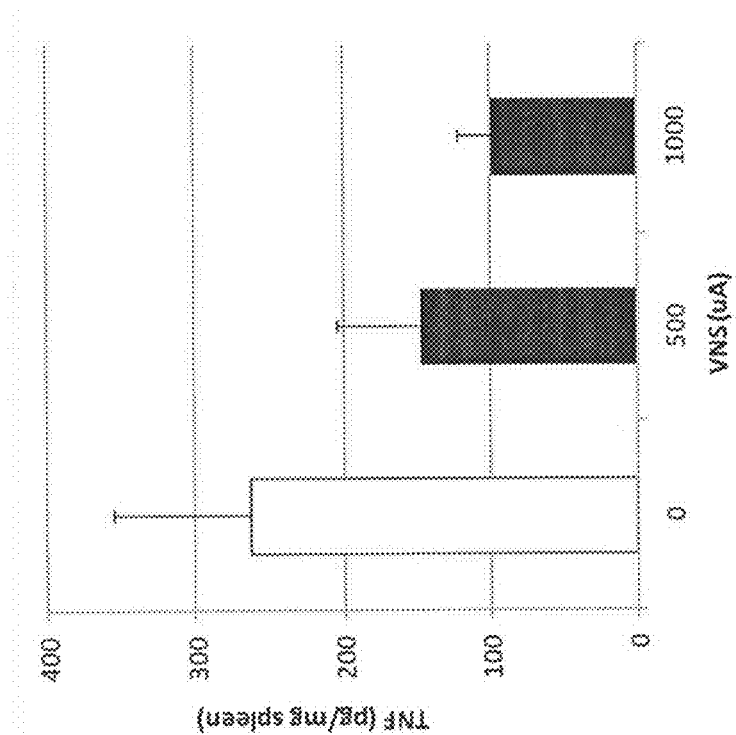
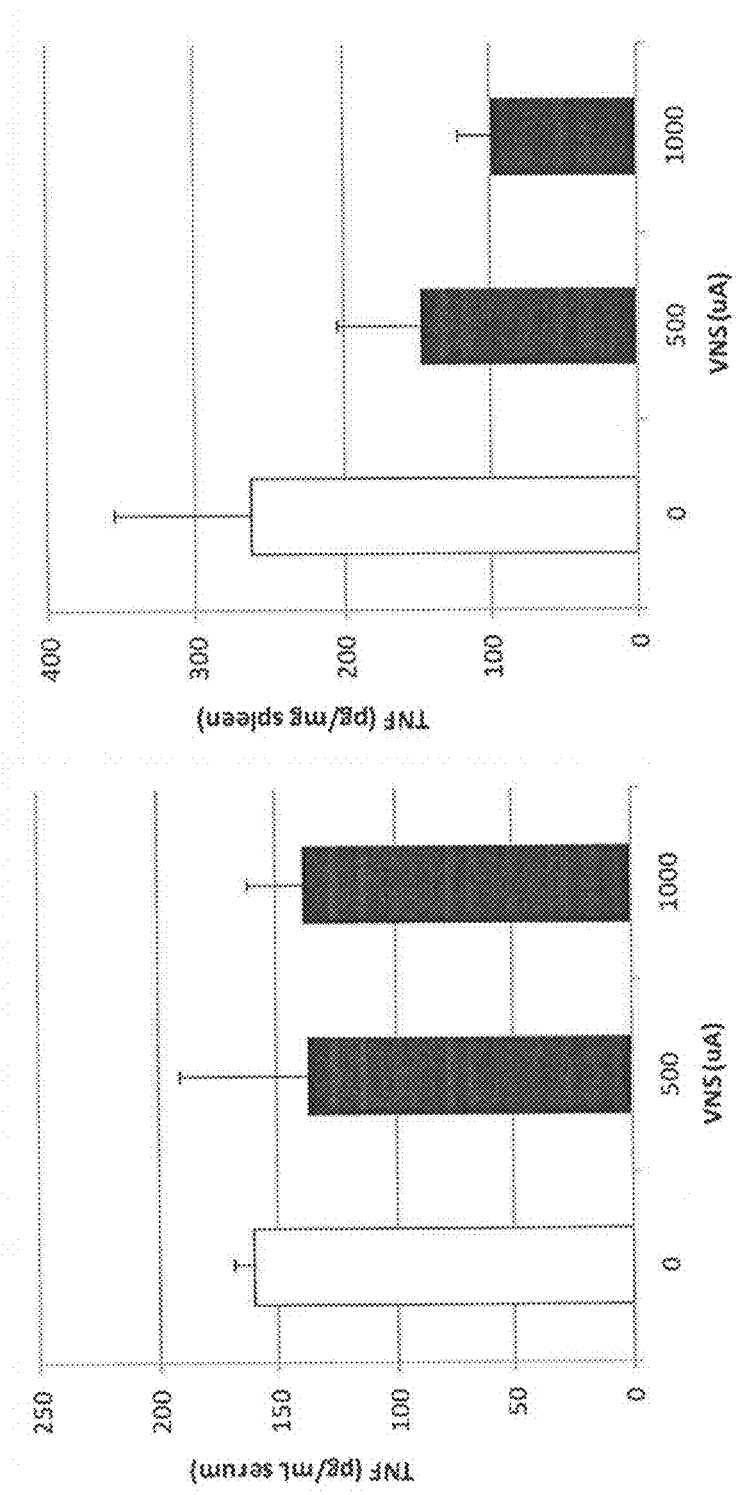
TNF is reduced in the spleen following VNS at both 500 and 1000 uA
FIG. 10A
FIG. 10B

MODULATION OF SIRTUINS BY VAGUS NERVE STIMULATION

CROSS REFERENCE TO RELATED APPLICATIONS

This application claims the benefit under 35 U.S.C. 119 of U.S. Provisional Patent Application No. 61/538,580, titled "MODULATION OF SIRTUINS BY VAGUS NERVE STIMULATION", filed on Sep. 23, 2011, and which is incorporated herein by reference in its entirety.

The following patent applications are also herein incorporated by reference in their entirety: U.S. patent application Ser. No. 12/434,462, titled "VAGUS NERVE STIMULATION ELECTRODES AND METHODS OF USE", filed on May 1, 2009, Publication No. US-2009-0275997-A1; U.S. patent application Ser. No. 12/620,413, titled "DEVICES AND METHODS FOR OPTIMIZING ELECTRODE PLACEMENT FOR ANTI-INFLAMATORY STIMULATION", filed on Nov. 17, 2009, Publication No. US-2010-0125304-A1; U.S. patent application Ser. No. 12/874,171, titled "PRESCRIPTION PAD FOR TREATMENT OF INFLAMMATORY DISORDERS", filed on Sep. 1, 2010, Publication No. US-2011-0054569-A1; U.S. patent application Ser. No. 12/917,197, titled "MODULATION OF THE CHOLINERGIC ANTI-INFLAMMATORY PATHWAY TO TREAT PAIN OR ADDICTION", filed on Nov. 1, 2010, Publication No. US-2011-0106208-A1; U.S. patent application Ser. No. 12/978,250, titled "NEURAL STIMULATION DEVICES AND SYSTEMS FOR TREATMENT OF CHRONIC INFLAMMATION", filed on Dec. 23, 2010, Publication No. US-2011-0190849-A1; U.S. patent application Ser. No. 12/797,452, titled "NERVE CUFF WITH POCKET FOR LEADLESS STIMULATOR", filed on Jun. 9, 2010, Publication No. US-2010-0312320-A1; U.S. patent application Ser. No. 10/446,625, titled "INHIBITION OF INFLAMMATORY CYTOKINE PRODUCTION BY CHOLINERGIC AGONISTS AND VAGUS NERVE STIMULATION", filed on May 28, 2003, now U.S. Pat. No. 6,838,471; U.S. patent application Ser. No. 10/375,696, titled "INHIBITION OF INFLAMMATORY CYTOKINE PRODUCTION BY STIMULATION OF BRAIN MUSCARINIC RECEPTORS", filed on Feb. 26, 2003, Publication No. US-2004-0048795-A1; U.S. patent application Ser. No. 11/807,493, titled "INHIBITION OF INFLAMMATORY CYTOKINE PRODUCTION BY STIMULATION OF BRAIN MUSCARINIC RECEPTORS", filed on May 29, 2007, Publication No. US-2008-0140138-A1; U.S. patent application Ser. No. 12/109,334, titled "INHIBITION OF INFLAMMATORY CYTOKINE PRODUCTION BY CHOLINERGIC AGONISTS AND VAGUS NERVE STIMULATION", filed on Apr. 24, 2008, Publication No. US-2009-0248097-A1; U.S. patent application Ser. No. 10/990,938, titled "INHIBITION OF INFLAMMATORY CYTOKINE PRODUCTION BY CHOLINERGIC AGONISTS AND VAGUS NERVE STIMULATION" filed on Nov. 17, 2004, Publication No. US-2005-0125044-A1; U.S. patent application Ser. No. 11/088,683, titled "NEURAL TOURNIQUET", filed on Mar. 24, 2005, Publication No. US-2005-0282906-A1; U.S. patent application Ser. No. 11/318,075, titled "TREATING INFLAMMATORY DISORDERS BY ELECTRICAL VAGUS NERVE STIMULATION", filed on Dec. 22, 2005, Publication No. US-2006-0178703-A1; U.S. patent application Ser. No. 12/259,208, titled "TREATING INFLAMMATORY DISORDERS BY STIMULATION OF THE CHOLINERGIC ANTI-INFLAMMATORY PATHWAY", filed on Oct. 27, 2008, Publication No. US-2009-0143831-A1; U.S. patent application Ser. No. 12/048,114, titled "TREATMENT OF INFLAMMATION BY NON-INVASIVE STIMULATION", filed on Mar. 13, 2008, Publication No. US-2008-0249439-A1; U.S. patent application Ser. No. 12/415,671, titled "METHODS AND SYSTEMS FOR REDUCING INFLAMMATION BY NEUROMODULATON OF T-CELL ACTIVITY", filed on Mar. 31, 2009, Publication No. US-2009-0247934-A1; and U.S. patent application Ser. No. 12/198,808, titled "DEVICES AND METHODS FOR INHIBITING GRANULOCYTE ACTIVATION BY NEURAL STIMULATION", filed on Aug. 26, 2008, Publication No. US-2009-0062874-A1.

The above referenced applications illustrate devices, compositions and methods of stimulating the vagus nerve to modulate the cholinergic anti-inflammatory pathway, including modulation of alpha-7 nicotinic acetylcholine receptors, and appropriate modulation of the vagus nerve (including electrical and/or mechanical modulation); such methods, devices and compositions are herein referenced with respect to modulation of the activity and/or level of sirtuins.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to systems, devices and methods for modulation of sirtuins by neurostimulation. In particular, sirtuins may be modulated by stimulation of the vagus nerve. Further described herein generally are methods and devices for modulating sirtuins, including agents (e.g., pharmacological agents) and implantable microstimulators, adapted for stimulating the vagus nerve to modulate sirtuins.

BACKGROUND

Stimulation of the vagus nerve, and particularly stimulation of the vagus nerve to modulate the neural cholinergic anti-inflammatory pathway (CAP or NCAP) has been described, beginning with the seminal work of Kevin Tracey (see, e.g., Tracey, K J "Physiology and immunology of the cholinergic antiinflammatory pathway." *The Journal of clinical investigation* 2007:117 (2): 289-96), who first identified the cholinergic anti-inflammatory pathway and characterized the link between vagus nerve stimulation and inhibition of inflammation by suppressing cytokine production. Since then, research has continued to explore the relationship between stimulation of the CAP and modulation of inflammatory disorders.

Surprisingly, as will be described in detail below, we have discovered that modulation of the vagus nerve may also modulate a family of proteins referred to as sirtuins. Silent information regulator (SIR) genes code for seven sirtuin enzymes (SIRT1 to SIRT7). These enzymes include deacetylases or mono-ADP-ribosyltransferases. Sirtuin enzymes are believed to be dependent on oxidized nicotinamide adenine dinucleotide (NAD+), an important metabolic coenzyme. Sirtuins have been shown to exert epigenetic effects resulting in manifold and disparate adaptogenic responses to stimuli, and are hypothesized to play an important role in response to stress and toxicity.

Sirtuin modulation has been shown to be beneficial in many disorders, such as age related disorders, obesity, heart disease, neurological function, and cancer. Lifespan extension in yeast and rodents have been linked to sirtuin activities. Unfortunately, there is an acknowledged problem with modulating sirtuin with pharmaceutical agonists across the blood-brain barrier. *N Engl J Med,* 2011 Jun. 9; 364(23): 2235-44.

The Sirt1 gene has been implicated in a host of cellular processes, and regulation of SIRT1 may modulate these processes. Sirt1 gene modulation may overlap with or converge on the neural cholinergic anti-inflammatory pathway (NCAP), as shown in FIG. 1 (adapted from Rahman and Islam: Mammalian Sirt1: insights on its biological functions. *Cell Communication and Signaling* 2011 9:11). The possible overlap between the NCAP pathways and the functions of the SIRT family of genes/enzymes is suggestive of a role of NCAP modulation techniques and methods (e.g., by stimulation of the vagus nerve or other components of the NCAP) in modulating Sirtuins.

We herein propose and describe for the first time a functional connection between the SIRT enzymes/genes and neuronal stimulation, and particularly vagal neuronal stimulation. In particular, we have found that sirtuin levels may be modulated (enhanced and in some variations suppressed) by specific and tailored stimulation of the vagus nerve. We further describe methods and systems for modulating sirtuins by stimulation of the vagus nerve based on these findings. Although modulation of sirtuins by neurostimulaion may be in some instances overlapping with modulation of the NCAP, the relationship between sirtuins and NCAP may be only partially coincident. For example, neurostimluation to modulate sirtuins may be optimized at different parameters than NCAP modulation. We herein propose methods of modulating sirtuins by analogy to NCAP, and in some variations by concurrent activation of NCAP. Further, NCAP stimulation to modulate inflammation may be more or less coincident with sirtuin modulation. Thus, we herein propose methods, devices and systems for modulating one or more SIRT family members by neurostimulation, including in some variations modulation of the NCAP, and/or stimulation of the vagus nerve.

SUMMARY OF THE DISCLOSURE

In general, described herein are methods, systems and devices for modulating sirtuins (SIRTs) in a patient. In particular, described herein are methods of electrically stimulating a subject's vagus nerve (VNS) to modulate one or more sirtuin, including subtypes of sirtuins (e.g., SIRT1, SIRT3, SIRT4, SIRT6, etc.), and/or sirtuins expressed in a subset of tissues (e.g., brain, heart, skin, liver, intestine, etc.). Modulations of Sirtuins may be modulated by the application of electrical energy to the vagus nerve, organs communicating with the vagus nerve, or portions of the vagus nerve (including afferent and efferent pathways).

Modulation may also refer to increase in sirtuin expression and/or activity, a decrease in sirtuin expression and/or activity, an uncoupling of the normal sirtuin response (e.g., inhibiting an increase and/or decrease in one or more sirtuin in response to a stimuli that would otherwise increase and/or decrease a sirtuin response), or the like. Modulation of sirtuin response may be sustained. For example, modulation may be provided on an ongoing basis by repeatedly stimulating the patient's vagus nerve (providing VNS); in general a very low duty cycle response may be provided, including providing an on-time (stimulation waveform) once per hour, once per four hours, once per six hours, once per eight hours, once per twelve hours, once per twenty-four hours, once per 48 hours, etc. The stimulation may be followed by an off-time during which no further electrical stimulation of the vagus nerve in a manner sufficient to modulation sirtuins is made (e.g., 2 hours, 4 hours, 6 hours, 8 hours, 12 hours, 24 hours, etc.).

For example, described herein are methods of modulating SIRT activity and/or level in a patient generally comprising modulating SIRT activity and/or level by applying electrical stimulation to a subject's vagus nerve. The simulation may be applied from an internal (e.g., implanted microstimulator) or external source. Although most of the examples herein describe electrical stimulation, in some variations other forms of stimulation may be used to modulate the Sirtuins by stimulation of the vagus nerve, including mechanical (including ultrasound), inductive, magnetic, chemical, and the like. In some variations, stimulation may result in excitation of the nerves or regions of the nerve fibers), which may be below threshold for activation of action potentials, or above threshold.

The step of applying may comprise applying stimulation from a microstimulator to the vagus nerve to modulate SIRT activity and/or level to treat any appropriate disorder. Treatments may include, for example: the treatment of cancer, to enhance longevity, to treat a metabolic syndrome, to treat or prevent liver cirrhosis/fatty liver, to treat or prevent muscle disorders such as Sarcopenia or disuse atrophy, to treat a circadian rhythm disorder, to treat insomnia, and/or to treat a CNS disorder including Alzheimer's, Parkinson's, or Huntington's diseases.

The method may also include the step of applying stimulation in conjunction with one or more active agents, including (but not limited to): drugs, medical food, probiotics. Drugs may be provided before, during or after treatment, and may enhance the electrical stimulation.

Appropriate waveforms for modulating sitruins may include electrical stimulation at a frequency, amplitude, pulsewidth, on-time, and off-time that is sufficient to modulate one or more (or in some cases, a specific subset of) sirtuins. For example in some variations the stimulation includes electrical stimulation by applying VNS having an amplitude of greater than about 500 μA, 750 μA, 1000 μA, 1500 μA, 2000 μA, etc. In one variation, the applied electrical stimulation comprises VNS having an amplitude of between about 150 μA and 5 mA, a pulse width of between about 50 μsec and 1 msec, a frequency of between about 1 Hz and 100 Hz, a duration of between about 1 sec and 5 min, an interpulse interval of between about 10 μsec and about 950 μsec.

As mentioned, the step of applying electrical stimulation may comprise applying electrical stimulation sufficient to modulate only a sub-set of SIRTs without substantially modulating another sub-set of SIRTs. For example, SIRT3 and/or SIRT4 may be modulated without substantially affecting SIRT1 and/or SIRT6. In some variations, all of the SIRTs may be modulated (e.g., SIRT1, SIRT3, SIRT4, and SIRT6). Additional members of the SIRT family may be modulated or not modulated by the applied VNS.

As mentioned the application of electrical stimulation may comprise applying repeated electrical stimulation separated by an off-time, including an off-time of greater than about 4 hours, 8 hours, 12 hours, etc. In general, the method of modulating sirtuins includes VNS stimulation by applying extremely low duty cycle electrical energy (e.g., an "on time" of less than 0.1 percent of the total time, less than 0.01 percent, less than 0.001 percent, etc.

The step of applying may comprise applying stimulation from the microstimulator to the vagus nerve to modify the patient's circadian cycles by modulating SIRT activity and/or level.

Also described herein are methods of treating a disorder by modulating SIRT activity and/or level in a patient, comprising modulating SIRT activity and/or level by applying electrical stimulation from a stimulator to stimulate the vagus nerve.

In any of the variations described herein, the method may include modifying the electrical stimulation based on feedback from one or more biomarker. For example, the feedback may be feedback from one or more of: SIRT and circadian rhythm biomarkers, etc. Feedback may be negative or positive; for example, the system may increase or decrease the electrical stimulation based on the feedback. The step of modifying the electrical stimulation may include modifying one or more of the time, duration, frequency, intensity, and/or interval of the electrical stimulation.

As mentioned, any of the methods described herein may also include applying electrical stimulation sufficient to modulate only a sub-set of SIRTs without substantially modulating another sub-set of SIRTs. For example, modulating SIRT activity and/or level may include modifying the activity and/or level of a plurality of different sirtuins. In one variation, the plurality of different sirtuins modulated includes SIRT1, SIRT3, SIRT4 and SIRT6. For example, the modulation of SIRT activity and/or level may include increasing the activity and/or level of a first sirtuin and decreasing the activity and/or level of a second sirtuin.

Further, the methods described herein for modulating sirtuins or treating a disorder by modulating sirtuins may also include coordinating the application of electrical stimulation from the stimulator based on the patient's circadian rhythm. Coordinating may comprise synchronization or asynchronization of electrical stimulation with circadian rhythm to modulate disease.

Also described herein are systems for treating a disorder in a patient by modulating SIRT, the system comprising: a stimulator configured to apply a low duty-cycle stimulation to a vagus nerve; and a controller configured to set a dose for the stimulator wherein the dose comprises a supra-threshold pulse followed by an off-period of greater than four hours configured to modulate SIRT level and/or activity. As mentioned, the stimulator may comprise an implantable microstimulator.

In some variations, the system includes a controller that is specifically configured drive the device to modulate sirtuins. For example, the controller may be configured to apply a waveform or waveforms at one or more of the treatment regimens descried herein to modulate sirtuins (e.g., having an amplitude of between about 150 µA and about 2 mA, etc.). In some variations, the system controller is configured to synchronize the applied stimulation with the patient's circadian rhythms. For example, the system or controller of the system may include feedback configured to indicate a subject's circadian rhythm.

BRIEF DESCRIPTION OF THE DRAWINGS

FIGS. 4A and 4B illustrate VNS up-regulation or maintenance of SIRT1 in heart and intestine (distal jejunum) in endotoxemia.

FIG. 5A illustrates VNS up-regulation or maintenance of SIRT3 in intestine (distal jejunum) in endotoxemia.

FIGS. 5B and 5C illustrates VNS up-regulation or maintenance of SIRT3 in fat in endotoxemia.

FIGS. 10A and 10B show the reduction in TNF in serum and spleen following VNS at different stimulation levels.

DETAILED DESCRIPTION

Figure 1:
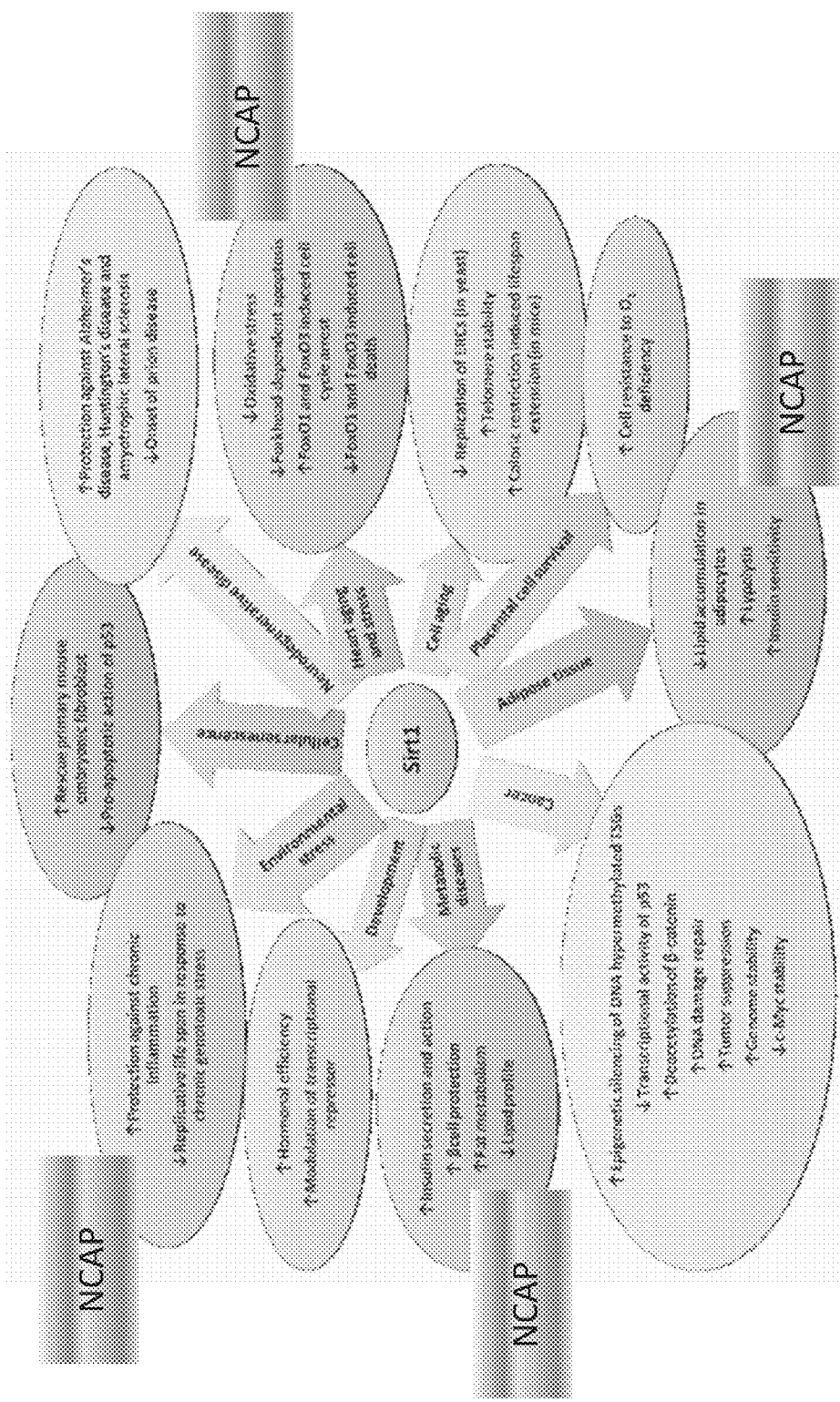
FIG. 1 illustrates various processes modulated by SIRT1 which overlap with the NCAP.

In general, described herein are methods, devices and systems for modulating sirtuin (SIRT) expression and/or activity by neurostimulation, including vagal nerve stimulation (VNS).

In some variations, the stimulation of the cholinergic anti-inflammatory pathway may be linked with (or coincide with) modulation of SIRT. In particular, stimulation of the vagus nerve at levels and ranges that are sufficient to reduce or prevent inflammation may also module SIRT expression/activity. For example, in some variations, methods of modulating one or more SIRT may be based on analogous NCAP stimulation. The potential overlap between the various therapeutic mechanisms of SIRT and NCAP may be exploited to treat a patient. For example, NCAP activation of CREB (and/or sirtuins) may contribute to long-term anti-inflammatory effect through CREB—sirtuin co-regulation. Further, NCAP has potential of activating sirtuin systems across the blood-brain barrier. As described in greater detail below, one or more sirtuins may be activated independently of the NCAP; that is stimulation effective for modulating sirtuins may not substantially modulate the NCAP.

It may also be possible and desirable to modulate one or more members of the SIRT family individually or collectively. As described in greater detail below, the stimulation parameters may be modulated to achieve this. For example, the stimulation waveform(s) (including pulse width, pulse duration, burst width, burst duration, current and/or voltage amplitude, on-time, off-time, polarity, and the like) may be modified, or the location of stimulation may be controlled (e.g., stimulation more or less afferently/efferently, stimulation of tissues innervated by the vagus nerve, stimulation at the carotid vagus nerve, etc.).

The NCAP has been previously linked to the alpha-7 nicotinic acetylcholine receptor (a7nAChR). In particular, a7nAChR interaction with type 6 adenylate cylcase up-regulated cAMP levels, and enhanced phosphorylation of CREB. Stimulation of the vagus nerve produced an a7nAChR-CREB dependent deactivated phenotype in monocytes. Sirt1 has been shown to modulate post-transcriptional regulation of CREB via a brain-specific microRNA, miR-134. Sirt1 normally functions to limit expression of miR-134 via a repressor complex containing the transcription factor YY1, and unchecked miR-134 expression following Sirt1 deficiency results in the downregulated expression of CREB and brain-derived neurotrophic factor (BDNF), thereby impairing synaptic plasticity. Further, Sirt1 expression is believed to be controlled by the activation of CREB. Thus, Sirt1 (and possibly other SIRT members) may be regulated by the level/activation of CREB. Modulation of CREB by the NCAP pathway may modulate SIRT activity.

In addition, NCAP may be linked to SIRT activity via NF-kB signaling. NF-kB is a rapid acting primary transcription factor that can be activated by, for example, inflammatory stimuli from microbial components or by endogenous inducers such as cytokines, spontaneous DNA breaks and other indicators of cellular stress. Once activated, NF-kB induces NF-kB target gene expression, leading to cellular aging, senescence, inflammation and/or insulin sensitivity. SIRT6 has been shown to interact with the NF-kB RELA subunit and to deacetylate histone H3 lysine 9 (H3K9) at NF-kB target gene promoters, thereby attenuating NF-kB signaling. Therefore, upregulating SIRT6 expression or activity may lead to increased attenuation of NF-kB signaling, which may reduce cellular aging and inflammation.

Sirtuins can bind acetylated proteins and NAD (see, e.g., Trends in Pharmacological Sciences, Volume 26, Issue 2, February 2005, Pages 94-103). Sirtuins use the energy of binding to the acetylated protein to twist the glycosidic bond between nicotinamide and ADP-ribose, thereby leading to a destabilized NAD conformation (Step 1). Following hydrolysis of the glycosidic bond, nicotinamide is released whereas ADP-ribose binds the acetyl-peptide with the formation of an O-alkylamidate intermediate (Step 20. The enzyme-intermediate complex eventually releases 2'-acetyl-ADP-ribose and the deacetylated proteins (Step 3). 2'-Acetyl-ADP-ribose in turn spontaneously equilibrates with the regioisomer 3'-acetyl-ADP-ribose through transesterification. Once released, nicotinamide can re-bind the O-alkylamidate intermediate driving the reverse reaction, leading to NAD re-synthesis (Step 2r).

Modulation of the NCAP may be adapted to modulate SIRT activity. For example, vagus nerve stimulation in a manner that modulates NCAP activity may modulate sirtuins. This modulation may be applied to treat diseases and disorders in which SIRT activity has been implicated, including those mentioned herein.

Further, pharmaceutical intervention of CAP activation, including acetylcholine and its analogues, and alpha7 nicotinic acetylcholine receptor agonists may be applied to modulate sirtuins, and therefore treat diseases and disorders in which SIRT activity has been implicated, including those mentioned herein. Other compounds, compositions and agents for modulating sirtuins are disclosed in U.S. Pat. No. 7,829,556 to Bemis et al. and U.S. Pat. No. 7,544,497 to Sinclair et al., which are herein incorporated by reference in their entireties. Examples of such compounds include resveratrol, a flavones, stilbene, flavanone, isoflavone, catechin, chalcone, tannin, anthocyanidin, nicotinamide, and sphingolipid such as sphingosine. These compounds, compositions and agents can be used in conjunction with VNS to modulate sirtuin levels in the patient's body. Combining VNS with administration of compounds, compositions and/or agents can allow greater control over the modulation of the sirtuin profiles of the patient. For example, VNS alone can result in the up-regulation of one or more members of the sirtuin family in a variety of tissues and the down-regulation of one or more members of the sirtuin family in some tissues. By additionally administering sirtuin modulating compounds, such as sirtuin agonists and/or sirtuin antagonists, the sirtuin profile after VNS can be further modulated or altered to, for example, increase activity of the VNS down-regulated members of the sirtuin family, and/or to further increase the activity of the VNS up-regulated members of the sirtuin family. The diseases or disorders for which modulation of SIRT by neurostimluation (e.g., including VNS modulation of CAP/NCAP), and in some embodiments co-administration of a SIRT modulating compound, may be used may include disorders/diseases that the cholinergic anti-inflammatory pathway has not been previously recognized as a therapeutic option, including (but not limited to): cancer prevention and treatment, longevity, CNS and other neurodegenerative disorders: Alzheimer's, Parkinson's Huntington's diseases (non-pharma method for modulating sirtuins in CNS), metabolic syndromes, liver cirrhosis/ fatty liver, muscle disorders: Sarcopenia, disuse atrophy, and insomnia (circadian rhythm disorders), stress related disorders, diabetes, obesity, chemotherapeutic induced neuropathy, neuropathy associated with an ischemic event, ocular diseases and/or disorders, inflammation, and/or flushing. Another example of a disorder that may be treated includes erectile dysfunction (ED). VNS alone or in combination with pharmacological agents (e.g., drugs) may be used to treat a disease/disorder. For example, VNS alone or in combination with phosphodiesterase type 5 inhibitors may be used to treat ED. Sirtuin-modulating methods and protocols that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. In other embodiments, sirtuin-modulating methods and protocols that decrease the level and/or activity of a sirtuin protein may be used for a variety of therapeutic applications including, for example, increasing cellular sensitivity to stress, increasing apoptosis, treatment of cancer, stimulation of appetite, and/or stimulation of weight gain, etc. As mentioned, inflammatory disorders (including any of those for which NCAP is indicated) may also be treated by modulation (and particularly electrical stimulation) of sirtuins as described herein.

Sirtuins are believed to have diverse physiological roles, and may be expressed or function in organ-specific ways. For example, SIRT1 has been shown to act with organ-specific physiology, along with some of the direct or indirect targets of sirtuin regulation. For example, SIRT1 activity has been shown in liver (e.g., regulating glucose production through TORC2, PGC-1alpha and FOXO1), pancreases (modulating insulin secretion via UCP-2), intestine (effecting tumor formation via beta-catenin activity), blood vessels (modulating angiogenesis and vascular tone, possibly through FOXO1 and eNOS, respectively), in fat tissue (effecting fat mobilization and lipid metabolism, possibly through PPAR-gamma and LXR, respectively), and in the brain (changing neuronal differentiation and increasing resistance to neurodegeneration by modulating apoptosis and/or through HCS1). Other SIRT family members may be differently implicated in other tissues and organs, and may be separately regulated, as discussed herein.

Examples of treatments for various indications are illustrated below. Any of these indications may be treated by electrical stimulation to modulate one or more sirtuins.

Aging/Stress

In one embodiment, the invention provides a method extending the lifespan of a cell, tissue or organ (or patient), extending the proliferative capacity of a cell tissue or organ, slowing aging of a cell tissue or organ, promoting the survival of a cell, tissue or organ, delaying cellular senescence in a cell, mimicking the effects of calorie restriction, increasing the resistance of a cell, tissue or organ to stress, or preventing apoptosis of a cell, by neuromodulation, such as VNS, alone or in combination with a compound, composition or agent.

In another embodiment, sirtuin-modulating methods and compounds that increase the level and/or activity of a sirtuin protein may be used to treat cells, tissues or organs (or entire patients) for transplantation or cell therapy, including, for example, solid tissue grafts, organ transplants, cell suspensions, stem cells, bone marrow cells, etc. The subject may be treated by VNS to modulate sirtuin levels before, during or after administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically by VNS to modulate sirtuin to increase the level and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In some embodiments, patients may be treated with a sirtuin-modulating method (e.g., VNS) to increase the level and/or activity of a sirtuin protein in vivo, e.g., to increase their lifespan or prevent apoptosis. For example, skin can be protected from aging (e.g., developing wrinkles, loss of elasticity, etc.) by treating with a sirtuin-modulating method that increases the level and/or activity of a sirtuin protein. In an exemplary embodiment, VNS is applied. The skin may also be contacted with a pharmaceutical or cosmetic composition that compliments or acts in conjunction with the increased sirtuin protein level/activity. Exemplary skin afflictions or skin conditions that may be treated in accordance with the methods described herein include disorders or diseases associated with or caused by inflammation, sun damage or natural aging. For example, the methods and compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, VNS that increase the level and/or activity of a sirtuin protein may be used for the treatment of wounds and/or burns to promote healing, including, for example, first-, second- or third-degree burns and/or a thermal, chemical or electrical burns.

VNS to increase the level and/or activity of a sirtuin protein may also be used as preventive, e.g., chemopreventive, compositions. When used in a chemopreventive method, susceptible skin is treated prior to any visible condition in a particular individual.

VNS may be delivered locally or systemically to a subject; for example, stimulation may be applied to a portion or region of the vagus nerve. In one embodiment, a sirtuin-modulating VNS is delivered locally by stimulating a sub-region of the VNS (e.g., more or less efferent); in other variations, the stimulation may be more centrally applied (e.g., near or above the cervical region of the VNS).

In another embodiment, VNS that modulates the level and/or activity of a sirtuin protein may be used for treating or preventing a disease or condition induced or exacerbated by cellular senescence in a subject. Thus described herein are methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death.

In yet another embodiment, VNS that increases the level and/or activity of a sirtuin protein may be administered to a subject in order to generally increase the lifespan of its cells and to protect its cells against stress and/or against apoptosis. It is believed that treating a subject with VNS (and optionally an additional compound) as described herein is similar to subjecting the subject to hormesis, i.e., mild stress that is beneficial to organisms and may extend their lifespan.

VNS may increase the level and/or activity of a sirtuin protein may be administered to a subject to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. VNS to modulate sirtuins (e.g., to increase the level and/or activity of a sirtuin protein) can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amniotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

VNS to modulate sirtuin protein level and/or activity can also be administered to a subject suffering from an acute disease, e.g., damage to an organ or tissue, e.g., a subject suffering from stroke or myocardial infarction or a subject suffering from a spinal cord injury. VNS to increase the level and/or activity of a sirtuin protein may also be used to repair an alcoholic's liver.

Cardiovascular Disease

In another embodiment, the invention provides a method for treating and/or preventing a cardiovascular disease by administering to a subject in need thereof VNS to modulate (e.g., increase/decrease) the level and/or activity of a sirtuin protein.

Cardiovascular diseases that can be treated or prevented using VNS may increase the level and/or activity of a sirtuin protein and may include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using VNS and optionally compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. VNS that increases the level and/or activity of a sirtuin protein may also be used for increasing HDL levels in plasma of an individual.

Yet other disorders that may be treated with VNS to modulate the level and/or activity of a sirtuin protein include restenosis, e.g., following coronary intervention, and disorders relating to an abnormal level of high density and low density cholesterol.

In one embodiment, appropriate VNS may increase the level and/or activity of a sirtuin protein and may be administered as part of a combination therapeutic with another cardiovascular agent. In one embodiment, VNS increases the level and/or activity of a sirtuin protein and may be administered as part of a combination therapeutic with an anti-arrhythmia agent. In another embodiment, VNS increases the level and/or activity of a sirtuin protein and may be administered as part of a combination therapeutic with another cardiovascular agent.

Cell Death/Cancer

Modulation of sirtuins by VNS to modulate the level and/or activity of a sirtuin protein may be administered to subjects who have recently received or are likely to receive a dose of radiation or toxin. In one embodiment, the dose of radiation or toxin is received as part of a work-related or medical procedure, e.g., administered as a prophylactic measure. In another embodiment, the radiation or toxin exposure is received unintentionally. In such a case, VNS is preferably administered as soon as possible after the exposure to inhibit apoptosis and the subsequent development of acute radiation syndrome.

VNS may also be used for treating and/or preventing cancer. In certain embodiments, VNS that increase the level and/or activity of a sirtuin protein may be used for treating and/or preventing cancer. Calorie restriction has been linked to a reduction in the incidence of age-related disorders including cancer. Accordingly, an increase in the level and/or activity of a sirtuin protein may be useful for treating and/or preventing the incidence of age-related disorders, such as, for example, cancer. Exemplary cancers that may be treated using VNS and optionally a sirtuin-modulating compound are those of the brain and kidney; hormone-dependent cancers including breast, prostate, testicular, and ovarian cancers; lymphomas, and leukemias. In cancers associated with solid tumors, VNS and one or more additional modulating compounds may be administered directly into the tumor. Cancer of blood cells, e.g., leukemia, can be treated by VNS. Benign cell growth, e.g., warts, can also be treated. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by VNS. Alternatively, cells can be obtained from a subject, treated ex vivo to remove certain undesirable cells, e.g., cancer cells, and administered back to the same or a different subject.

Chemotherapeutic agents may be co-administered with modulating compounds described herein as having anti-cancer activity, e.g., compounds that induce apoptosis, compounds that reduce lifespan or compounds that render cells sensitive to stress. Chemotherapeutic agents may be used with VNS as described herein for inducing cell death or reducing lifespan or increasing sensitivity to stress and/or in combination with other chemotherapeutics agents. In addition to conventional chemotherapeutics, VNS and the sirtuin-modulating compounds described herein may also be used with antisense RNA, RNAi or other polynucleotides to inhibit the expression of the cellular components that contribute to unwanted cellular proliferation.

Combination therapies comprising VNS to modulate sirtuins and a conventional chemotherapeutic agent may be advantageous over combination therapies known in the art because the combination allows the conventional chemotherapeutic agent to exert greater effect at lower dosage. In a preferred embodiment, the effective dose ($ED_{50}$) for a chemotherapeutic agent, or combination of conventional chemotherapeutic agents, when used in combination with VNS to modulate sirtuins may be at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with VNS described herein can be at least 2 fold greater than the TI for conventional chemotherapeutic regimen alone, and even more preferably at 5 fold, 10 fold or even 25 fold greater.

Neuronal Diseases/Disorders

In certain aspects, VNS that increase the level and/or activity of a sirtuin protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. VNS that modulates the level and/or activity of a sirtuin protein can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g. glial cells) between them. The earliest symptoms include loss of recent memory, faulty judgment, and changes in personality. PD is a CNS disorder that results in uncontrolled body movements, rigidity, tremor, and dyskinesia, and is associated with the death of brain cells in an area of the brain that produces dopamine. ALS (motor neuron disease) is a CNS disorder that attacks the motor neurons, components of the CNS that connect the brain to the skeletal muscles.

HD is another neurodegenerative disease that causes uncontrolled movements, loss of intellectual faculties, and emotional disturbance. Tay-Sachs disease and Sandhoff disease are glycolipid storage diseases where GM2 ganglioside and related glycolipidssubstrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with VNS to modulate sirtuins.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. VNS that increases the level and/or activity of a sirtuin protein may be useful for treating or preventing neuronal loss due to these prior diseases.

In another embodiment, VNS that increases or decreases the level and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, VNS that modulates the level and/or activity of a sirtuin protein may be used to treat or prevent multiple sclerosis (MS), including relapsing MS and monosymptomatic MS, and other demyelinating conditions, such as, for example, chronic inflammatory demyelinating polyneuropathy (CIDP), or symptoms associated therewith.

In yet another embodiment, VNS that modulates the level and/or activity of a sirtuin protein may be used to treat trauma to the nerves, including, trauma due to disease, injury (including surgical intervention), or environmental trauma (e.g., neurotoxins, alcoholism, etc.).

VNS that modulates the level and/or activity of a sirtuin protein may also be useful to prevent, treat, and alleviate symptoms of various PNS disorders. The term "peripheral neuropathy" encompasses a wide range of disorders in which the nerves outside of the brain and spinal cord— peripheral nerves—have been damaged. Peripheral neuropathy may also be referred to as peripheral neuritis, or if many nerves are involved, the terms polyneuropathy or polyneuritis may be used.

PNS diseases treatable with VNS modulation of the level and/or activity of a sirtuin protein include: diabetes, leprosy, Charcot-Marie-Tooth disease, Guillain-Barre syndrome and Brachial Plexus Neuropathies (diseases of the cervical and first thoracic roots, nerve trunks, cords, and peripheral nerve components of the brachial plexus.

In another embodiment, VNS modulation of sirtuins may be used to treat or prevent a polyglutamine disease. Exemplary polyglutamine diseases include Spinobulbar muscular atrophy (Kennedy disease), Huntington's Disease (HD), Dentatorubral-pallidoluysian atrophy (Haw River syndrome), Spinocerebellar ataxia type 1, Spinocerebellar ataxia type 2, Spinocerebellar ataxia type 3 (Machado-Joseph disease), Spinocerebellar ataxia type 6, Spinocerebellar ataxia type 7, and Spinocerebellar ataxia type 17.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. In one embodiment, apoptotic or necrotic cell death may be prevented. In still a further embodiment, ischemic-mediated damage, such as cytoxic edema or central nervous system tissue anoxemia, may be prevented. In each embodiment, the central nervous system cell may be a spinal cell or a brain cell.

Another aspect encompasses administrating VNS modulation of sirtuins of a subject to treat a central nervous system ischemic condition. A number of central nervous system ischemic conditions may be treated by VNS. In one embodiment, the ischemic condition is a stroke that results in any type of ischemic central nervous system damage, such as apoptotic or necrotic cell death, cytoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, VNS modulation of sirtuins may be administered to reduce infarct size of the ischemic core following a central nervous system ischemic condition. Moreover, VNS modulation of sirtuins may also be beneficially administered to reduce the size of the ischemic penumbra or transitional zone following a central nervous system ischemic condition.

In one embodiment, a combination VNS and drug regimen may include drugs or compounds for the treatment or prevention of neurodegenerative disorders or secondary conditions associated with these conditions. Thus, a combination VNS and drug regimen may include one or more anti-neurodegeneration agents.

Blood Coagulation Disorders

In other aspects, VNS modulation of sirtuin proteins can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering VNS to modulate the level and/or activity of a sirtuin protein. VNS and the methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites.

In another embodiment, VNS modulation of sirtuins may include drugs or compounds for the treatment or prevention of blood coagulation disorders or secondary conditions associated with these conditions. Thus, a combination drug regimen may include modulation of sirtuins by VNS to increase the level and/or activity of a sirtuin protein and one or more anti-coagulation or anti-thrombosis agents.

Weight Control

In another aspect, VNS that increase or decreases the level and/or activity of a sirtuin protein may be used for treating or preventing weight gain or obesity in a subject. For example, VNS modulation of sirtuins may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, VNS modulation of sirtuins may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem). Finally, patients with AIDS can develop lipodystrophy or insulin resistance in response to combination therapies for AIDS.

In another embodiment, VNS that increases or decreases the level and/or activity of a sirtuin protein may be used for inhibiting adipogenesis or fat cell differentiation, whether in vitro or in vivo. Such methods may be used for treating or preventing obesity.

In other embodiments, VNS that modulates the level and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese.

In any of the methods of treatment described herein, the method may comprise VNS modulation of sirtuins administered regularly in an ongoing fashion (e.g., hourly, daily or, every other day, or once a week), or in an on-demand or triggered manner (e.g., triggered by patient or physician control, triggered by detection of a monitored parameter, etc.).

In an exemplary embodiment, VNS that modulates the level and/or activity of a sirtuin protein may be administered as a combination therapy for treating or preventing weight gain or obesity. For example, VNS may be administered in combination with one or more anti-obesity agents.

In another embodiment, VNS modulation of sirtuins may be administered to reduce drug-induced weight gain. For example, VNS may increase the level and/or activity of a sirtuin protein may be administered as a combination therapy with medications that may stimulate appetite or cause weight gain, in particular, weight gain due to factors other than water retention.

Metabolic Disorders/Diabetes

In another aspect, VNS that modulates the level and/or activity of a sirtuin protein may be used for treating or preventing a metabolic disorder, such as insulin-resistance, a pre-diabetic state, type II diabetes, and/or complications thereof. For example, administration of VNS modulation of sirtuins that increases the level and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, VNS that increases the level and/or activity of a sirtuin protein may be administered as a combination therapy for treating or preventing a metabolic disorder. For example, VNS modulation of sirtuins may be administered in combination with one or more anti-diabetic agents.

Inflammatory Diseases

In other aspects, VNS modulation of sirtuins can be used to treat or prevent a disease or disorder associated with inflammation. For example, VNS that increases the level and/or activity of a sirtuin protein may be administered prior to the onset of, at, or after the initiation of inflammation. When used prophylactically, VNS modulation of sirtuins may preferably be provided in advance of any inflammatory response or symptom. Administration of VNS may prevent or attenuate inflammatory responses or symptoms.

In another embodiment, VNS that modulates the level and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). VNS modulation of sirtuins may be used to treat chronic hepatitis infection, including hepatitis B and hepatitis C.

Additionally, VNS that modulates the level and/or activity of a sirtuin protein may be used to treat autoimmune diseases and/or inflammation associated with autoimmune diseases such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In certain embodiments, VNS modulation of sirtuins may be taken alone or in combination with other compounds useful for treating or preventing inflammation.

Flushing

In another aspect, VNS that modulates the level and/or activity of a sirtuin protein may be used for reducing the incidence or severity of flushing and/or hot flashes which are symptoms of a disorder. For instance, the subject method includes the use of VNS that increases the level and/or activity of a sirtuin protein, alone or in combination with other agents, for reducing incidence or severity of flushing and/or hot flashes in cancer patients. In other embodiments, the method provides for the use of VNS that increases the level and/or activity of a sirtuin protein to reduce the incidence or severity of flushing and/or hot flashes in menopausal and post-menopausal woman.

In another aspect, VNS that modulates the level and/or activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof VNS and optionally a formulation comprising at least one flushing inducing compound. In other embodiments, a method for treating drug induced flushing comprises separately administering VNS and optionally one or more compounds that induce flushing. The sirtuin-modulating VNS may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, faloxifene, antidepressants, anti-psychotics, chemotherapeutics, calcium channel blockers, and antibiotics.

In one embodiment, VNS that modulates the level and/or activity of a sirtuin protein may be used to reduce flushing side effects of a vasodilator or an antilipemic agent (including anticholesteremic agents and lipotropic agents). In an exemplary embodiment, VNS modulation of sirtuins may be used to reduce flushing associated with the administration of niacin.

In another embodiment, the invention provides a method for treating and/or preventing hyperlipidemia with reduced flushing side effects. In another representative embodiment, the method involves the use of VNS that modulates (e.g., increases, decreases, etc.) the level and/or activity of a sirtuin protein to reduce flushing side effects of raloxifene. In another representative embodiment, the method involves the use of VNS that increases the level and/or activity of a sirtuin protein to reduce flushing side effects of antidepressants or anti-psychotic agent. For instance, VNS that increases the level and/or activity of a sirtuin protein can be used in conjunction (administered separately or together) with a serotonin reuptake inhibitor, or a 5HT2 receptor antagonist.

In certain embodiments, VNS modulation of sirtuins may be used as part of a treatment with a serotonin reuptake inhibitor (SRI) to reduce flushing. In still another representative embodiment, VNS that increases the level and/or activity of a sirtuin protein may be used to reduce flushing side effects of chemotherapeutic agents, such as cyclophosphamide and tamoxifen.

In another embodiment, VNS modulation of sirtuins may be used to reduce flushing side effects of calcium channel blockers, such as amlodipine.

In another embodiment, VNS that increases the level and/or activity of a sirtuin protein may be used to reduce flushing side effects of antibiotics. For example, sirtuin-modulating compounds that increase or decrease the level and/or activity of a sirtuin protein can be used in combination with levofloxacin.

Ocular Disorders

One aspect of the present invention is a method for inhibiting, reducing or otherwise treating vision impairment by administering to a patient VNS modulation of sirtuins.

In certain aspects of the invention, the vision impairment is caused by damage to the optic nerve or central nervous system. In particular embodiments, optic nerve damage is caused by high intraocular pressure, such as that created by glaucoma. In other particular embodiments, optic nerve damage is caused by swelling of the nerve, which is often associated with an infection or an immune (e.g., autoimmune) response such as in optic neuritis.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disruption of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g. conjunctivitis, keratitis, tuberculosis, syphilis, gonorrhea), viral infections (e.g. Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g. *Candida choroiditis*, histoplasmosis), protozoal infections (e.g. toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, a drug that raises intraocular pressure such as a steroid), by administering to the subject in need of such treatment VNS modulation of sirtuins as disclosed herein.

Another aspect of the invention is a method for inhibiting, reducing or treating vision impairment in a subject undergoing surgery, including ocular or other surgeries performed in the prone position such as spinal cord surgery, by administering to the subject in need of such treatment VNS modulation of sirtuins as disclosed herein. Ocular surgeries include cataract, iridotomy and lens replacements.

Another aspect of the invention is the treatment, including inhibition and prophylactic treatment, of age related ocular diseases include cataracts, dry eye, age-related macular degeneration (AMD), retinal damage and the like, by administering to the subject in need of such treatment VNS modulation of sirtuins.

Another aspect of the invention is the prevention or treatment of damage to the eye caused by stress, chemical insult or radiation, by administering to the subject in need of such treatment VNS modulation of sirtuins. Radiation or electromagnetic damage to the eye can include that caused by CRT's or exposure to sunlight or UV.

In one embodiment, a combination drug regimen may include drugs or compounds for the treatment or prevention of ocular disorders or secondary conditions associated with these conditions. Thus, a combination drug regimen may include modulation of sirtuins by VNS and one or more therapeutic agents for the treatment of an ocular disorder.

In one embodiment, VNS modulation of sirtuins in conjunction with a therapy for reducing intraocular pressure. In another embodiment, VNS modulation of sirtuins can be administered in conjunction with a therapy for treating and/or preventing glaucoma. In yet another embodiment, VNS modulation of sirtuins can be administered in conjunction with a therapy for treating and/or preventing optic neuritis. In one embodiment, VNS modulation of sirtuins can be administered in conjunction with a therapy for treating and/or preventing CMV Retinopathy. In another embodiment, VNS modulation of sirtuins can be administered in conjunction with a therapy for treating and/or preventing multiple sclerosis.

Mitochondrial-Associated Diseases and Disorders

In certain embodiments, the invention provides methods for treating diseases or disorders that would benefit from increased mitochondrial activity. The methods involve administering to a subject in need thereof VNS modulation of sirtuins. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

In certain embodiments, methods for treating diseases or disorders that would benefit from increased mitochondrial activity may comprise identifying a subject suffering from a mitochondrial dysfunction. Methods for diagnosing a mitochondrial dysfunction may involve molecular genetic, pathologic and/or biochemical analyses. Diseases and disorders associated with mitochondrial dysfunction include diseases and disorders in which deficits in mitochondrial respiratory chain activity contribute to the development of pathophysiology of such diseases or disorders in a mammal. Diseases or disorders that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis.

In certain embodiments, the invention provides methods for treating a disease or disorder that would benefit from increased mitochondrial activity that involves administering to a subject in need thereof VNS modulation of sirtuins in combination with another therapeutic agent such as, for example, an agent useful for treating mitochondrial dysfunction or an agent useful for reducing a symptom associated with a disease or disorder involving mitochondrial dysfunction.

In exemplary embodiments, the invention provides methods for treating diseases or disorders that would benefit from increased mitochondrial activity by administering to a subject VNS modulation of sirtuins. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

Muscular dystrophy refers to a family of diseases involving deterioration of neuromuscular structure and function, often resulting in atrophy of skeletal muscle and myocardial dysfunction, such as Duchenne muscular dystrophy. In certain embodiments, VNS may be used for reducing the rate of decline in muscular functional capacities and for improving muscular functional status in patients with muscular dystrophy.

In certain embodiments, VNS modulation of sirtuins may be useful for treatment mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external opthalmoplegia, the Kearns-Sayre syndrome (with opthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal).

In certain embodiments, VNS modulation of sirtuins may be useful for treating patients suffering from toxic damage to mitochondria, such as, toxic damage due to calcium accumulation, excitotoxicity, nitric oxide exposure, drug induced toxic damage, or hypoxia.

In certain embodiments, VNS modulation of sirtuins may be useful for treating diseases or disorders associated with mitochondrial deregulation.

Muscle Performance

In other embodiments, the invention provides methods for enhancing muscle performance by administering VNS modulation of sirtuins. For example, VNS may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering VNS to increase mitochondrial activity, increase mitochondrial biogenesis, and/or increase mitochondrial mass.

Sports performance refers to the ability of the athlete's muscles to perform when participating in sports activities. Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc. Enhanced sports performance in manifested by the ability to overcome muscle fatigue, ability to maintain activity for longer periods of time, and have a more effective workout.

In the arena of athlete muscle performance, it is desirable to create conditions that permit competition or training at higher levels of resistance for a prolonged period of time.

It is contemplated that the methods of the present invention will also be effective in the treatment of muscle related pathological conditions, including acute sarcopenia, for example, muscle atrophy and/or cachexia associated with burns, bed rest, limb immobilization, or major thoracic, abdominal, and/or orthopedic surgery.

In certain embodiments, the invention provides VNS modulation of sirtuins, devices, systems and methods of modulation of sirtuins for improvement of sports performance. Accordingly, provided are therapeutic methods and systems that have actions of improving physical endurance and/or inhibiting physical fatigues for those people involved in broadly-defined exercises including sports requiring endurance and labors requiring repeated muscle exertions. Such dietary compositions may additional comprise electrolytes, caffeine, vitamins, carbohydrates, etc.

Other Uses

VNS that modulates the level and/or activity of a sirtuin protein may be used for treating or preventing viral infections (such as infections by influenza, herpes or papilloma virus) or as antifungal agents. In certain embodiments, VNS that increases or decreases the level and/or activity of a sirtuin protein may be administered as part of a combination drug therapy with another therapeutic agent for the treatment of viral diseases. In another embodiment, VNS that increases the level and/or activity of a sirtuin protein may be administered as part of a combination drug therapy with another anti-fungal agent.

Subjects that may be treated as described herein include eukaryotes, such as mammals, e.g., humans, ovines, bovines, equines, porcines, canines, felines, non-human primate, mice, and rats. For example, VNS modulation of sirtuins may be administered to farm animals to improve their ability to withstand farming conditions longer.

At least in view of the link between reproduction and longevity, VNS that increases the level and/or activity of a sirtuin protein can be applied to affect the reproduction of animals.

Neuromodulation of Sirtuins

The methods described herein apply various stimulation protocols that were previously described (see, in particular, the listing of patents and patent applications listed above, and incorporated herein by reference in their entirety) as used to significantly reduce inflammation and/or the effects of inflammation. For example, electrical simulation may be used. The parameters of an applied electrical stimulation to modulate SIRT expression/activity include the location of stimulation, which may include the vagus nerve or other portions of the neuronal anti-inflammatory pathway. In some embodiments, stimulation can be limited to either the afferent fibers of the vagus nerve or the efferent fibers of the vagus nerve, while in other embodiments, both the afferent fibers and the efferent fibers of the vagus nerve can be stimulated. In addition, other tissues that influence vagus nerve activity can be stimulated, such as tissues of the esophagus, stomach, small and large intestines, pancreas, liver, gallbladder, kidney, mesentery, appendix, bladder, uterus, and other intraabdominal tissues. Stimulation of these additional tissues can allow modulation of the activity of the afferent fibers of the vagus nerve without significantly activating efferent fibers of the vagus nerve. Further examples of additional tissues and nerves that can be stimulated or modulated are disclosed in U.S. Pat. No. 7,599,736, which is hereby incorporated by reference it its entirety.

The parameters of stimulation may also include the electrical parameters, such as the pulse shape (e.g., sinusoidal, square, biphasic, monophasic, etc.) the duration of stimulation, the on-time, the off-time, the inter-pulse interval, or the like. One factor examined herein is the number of supra-threshold pulses. The stimulation of the vagus nerve with even a single supra-threshold stimulus has been shown to result in a significant and long-lasting effect on inflammatory cytokines, even when compared to multiple stimulations; we herein propose such stimulation may also affect SIRT activity/levels.

The examples described herein use a stimulator and stimulation control package that was developed for use in driving vagus nerve stimulation. In some examples, the stimulation is controlled by a software package that is configured to run on a microprocessor (e.g., personal computer) and to control output of an emulator/stimulator (which may be referred to as an "ITE" emulator stimulator).

Parameters controlling stimulation and data acquisition may include: (1) selected stimulating electrode pair including a cathode and anode; (2) frequency in 1 Hz increments; (3) Pulse Width (PW): e.g., 20-2,000 uS in 1 uS increments; (4) Pulse Amplitude (PA): e.g., ±0-5,000 uA in 3 uA increments; and (5) Inter-Pulse-Interval between phase A & B of waveform (IPI): e.g., 20-2,000 uS in 1 uS increments.

For example, an exemplary waveform may be a biphasic (charge balanced) waveform that includes two symmetric pulse widths (PW, one positive, one negative) separated by an inter-pulse interval (IPI). The pulse widths may have a pulse amplitude (PA) that is also symmetric for the first phase (phase A) and the second phase (phase B) of the biphasic stimulus. Other pulse waveforms may be used.

A stimulator may be used to generate a pulse train on a pair of electrodes. The pulses may be generated using a bipolar current source and can be capacitively isolated with >1 uF ceramic capacitors on both electrodes outputs. Compliance voltage can be set to as high as +/−18.8 volts.

In one example, electrodes (e.g., cuff electrodes 0.3 mm ID, 0.5 mm inter-electrode distance; Microprobes, Gaithersburg, Md.) may be implanted and placed around or near the vagus nerve to apply stimulus to the vagus nerve. Supra-threshold pulses (750 µA, 200 µS, 10 Hz) may be applied in various numbers (0, 1, 10, 100, 300, 600, 3000). Other commercially available electrodes for use in vagus nerve stimulation include vagus nerve stimulators made by Cyberonics. In other embodiments, other suitable electrode configurations can be used, such as a needle electrode, for example, which can be implanted transcutaneously through the skin and into the vagus nerve. In other embodiments, the electrodes are not implanted.

By analogy to the NCAP inflammatory effects previously described, the application of even a single brief supra-threshold stimulus of the vagus nerve may result in a substantial modulation of the effects and/or levels of SIRT (e.g., SIRT1). However, the modification of the sirtuins by neuronal stimulation may be differently regulated than the NCAP modulation. Thus neuronal stimulation resulting in a modulation of the NCAP may not substantially modify sirtuins, or vice versa. For example, a brief supra-threshold stimulus may affect NCAP but not substantially affect SIRT.

Any of the methods described herein may be used to treat a patient for one or more disorders by specifically and/or selectively modulating SIRT levels. Specificity may be provided by modulating the stimulation (e.g., the stimulation parameters, including, but not limited to: time, duration, frequency, intensity, and/or interval of the stimulation). In some variations a burst of pulses may be used, followed by an off-time interval; the off-time interval, compared to the "on time" or stimulation time, may be very large, one the order of minutes, hours or days, so that the stimulation may be extremely low duty cycle.

In some variations the modulation of SIRT may be performed by stimulation that is modulated by feedback from the patient, including feedback from the patient's SIRT level(s), and/or other biomarkers, such as markers of circadian rhythms.

In some variations, the stimulation may be coordinated with the patient's circadian rhythms. For example, the stimulation may be applied in synchronization with the patient's circadian rhythm to modulate sirtuins and treat disease. Alternatively, the stimulation may be applied asynchronously with circadian rhythm to treat a disorder or disease.

Examples of SIRT Modulation

FIGS. 2 through 9 illustrate the modulation of SIRT by neurostimuation. In this example, SIRT is modulated (e.g., the protein levels are modified) by VNS. BALB/c male mice were anesthetized with Ketamine/xylazine followed by VNS or sham VNS. The mice in many of these examples were fitted with a cuff electrode around their left carotid sheath, and square, charge-balanced biphasic pulses were applied through the bipolar cuff electrode. The stimulation (VNS) protocol consisted of applying a 1 mA, 200 µm pulse width, 10 Hz, 60 S, 50 uS interpulse-interval waveform, using a modified stimulation having an 18.8V supply. Mice were allowed to recover for 3 hrs, and were then challenged with IP injection of 10 mg/kg lipopolysaccharide (LPS) or carrier (saline). These stimulation parameters (electrical stimulation parameters) may be varied to differently modulate the sirtuin response. Other stimulation parameters were also examined, as illustrated below.

Thereafter, the mice were euthanized 90 minutes post LPS-challenge (4.5 hr post VNS), and various organs harvested for analysis. Harvest organs were homogenized in cold TPER with a protease inhibitor cocktail. SIRT1 and SIRT3 was thereafter measured for the different tissues by Western Blot (Primary rabbit antibody to either: SIRT1:sc-15404; or SIRT3: sc-sc-99143 (Santa Cruz Biotech). Secondary antibody was IRDye680 Goat Anti-Rabbit IgG (Li-cor Biosciences). Non-LPS challenged mice (with or without VNS, n=1) were used as a control, and LPS challenged mice (with or without VNS, n=2) were also examined.

Figure 2:
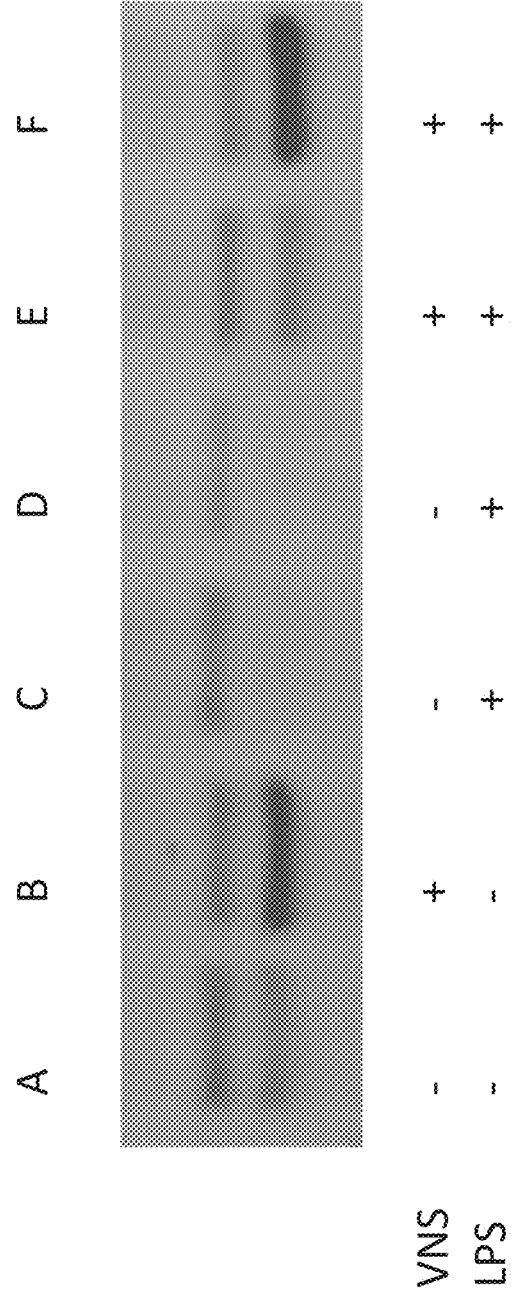
FIG. 2 illustrates VNS up-regulation of SIRT1 in (epididymal) fat and prevention of loss of SIRT1 in an endotoxemia model.

FIG. 2 shows the results of one variation of this experiment. In this case, SIRT1 levels were low or at a basal level in the white fat of unchallenged mice, and VNS increases a SIRT fraction of greater electrophoretic mobility, likely a variable post-translationally modified state of SIRT1 (Lanes A, B) or de novo synthesis. In white fat of LPS challenged mice, SIRT1 levels are seen as decreased in FIG. 2 (Lanes C, D). This may contribute to glucose disregulation in endotoxemia (as did SIRT1 decrease in liver after LPS challenge J Biol Chem. 2010 Dec. 31; 285(53):41391-401). Finally, VNS prevents loss or reduces the loss of SIRT1 in white fat in endotoxemia (Lanes E, F). Note that the upper and lower bands both reflect SIRT1 (and may indicate conformational variation).

In general, the term "modulation" in reference to modulation of sirloins may refer to an increase or decrease in sirtuin levels following stimulation; the stimulation may be the electrical stimulation, or it may be following an evoked stimulation of the patient that would otherwise result in a change in sirtuin level. For example, a baseline (or normal) response may result in an increase in expression or activity of sirtuin following a trigger such as stimulation by LPS (endotoxemia). This normal sirtuin response may be modulated by VNS so that the response is greater or lesser than it would otherwise be.

Figure 3:
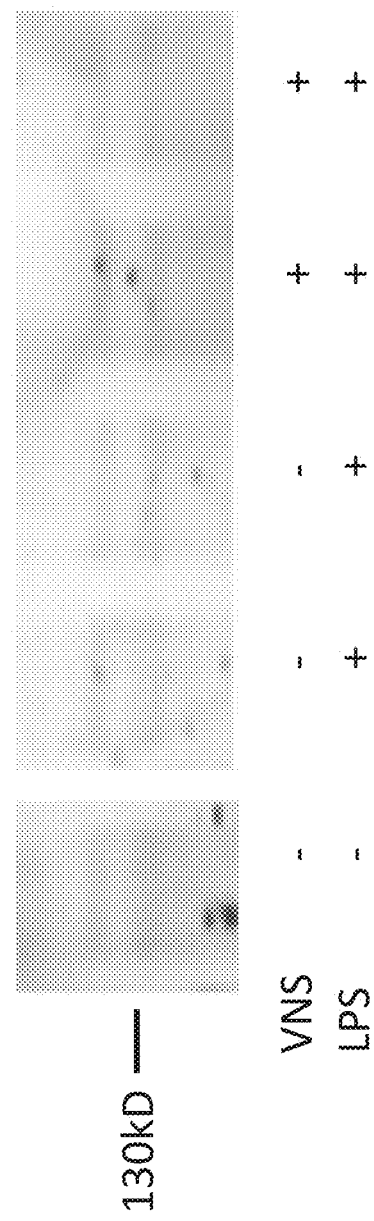
FIG. 3 shows VNS up-regulates or maintains SIRT1 in pancreas during endotoxemia.

FIG. 3 shows that VNS up-regulates or maintains SIRT1 in pancreas during endotoxemia. In this example, the western blot shows the effect of VNS on SIRT levels in pancreas after endotoxemia challenge. FIGS. 4A and 4B show a similar up-regulation or maintenance of SIRT1 in heart and intestine (distal jejunum) in endotoxemia.

FIG. 5A shows a large effect of VNS in up-regulating and/or maintenance of SIRT3 in intestine (distal jejunum) in endotoxemia. FIG. 5B shows that VNS up-regulates and/or maintains SIRT3 levels in fat in endotoxemia. FIG. 5C shows that VNS up-regulates SIRT3 levels in fat in unchallenged mice.

Figure 6:
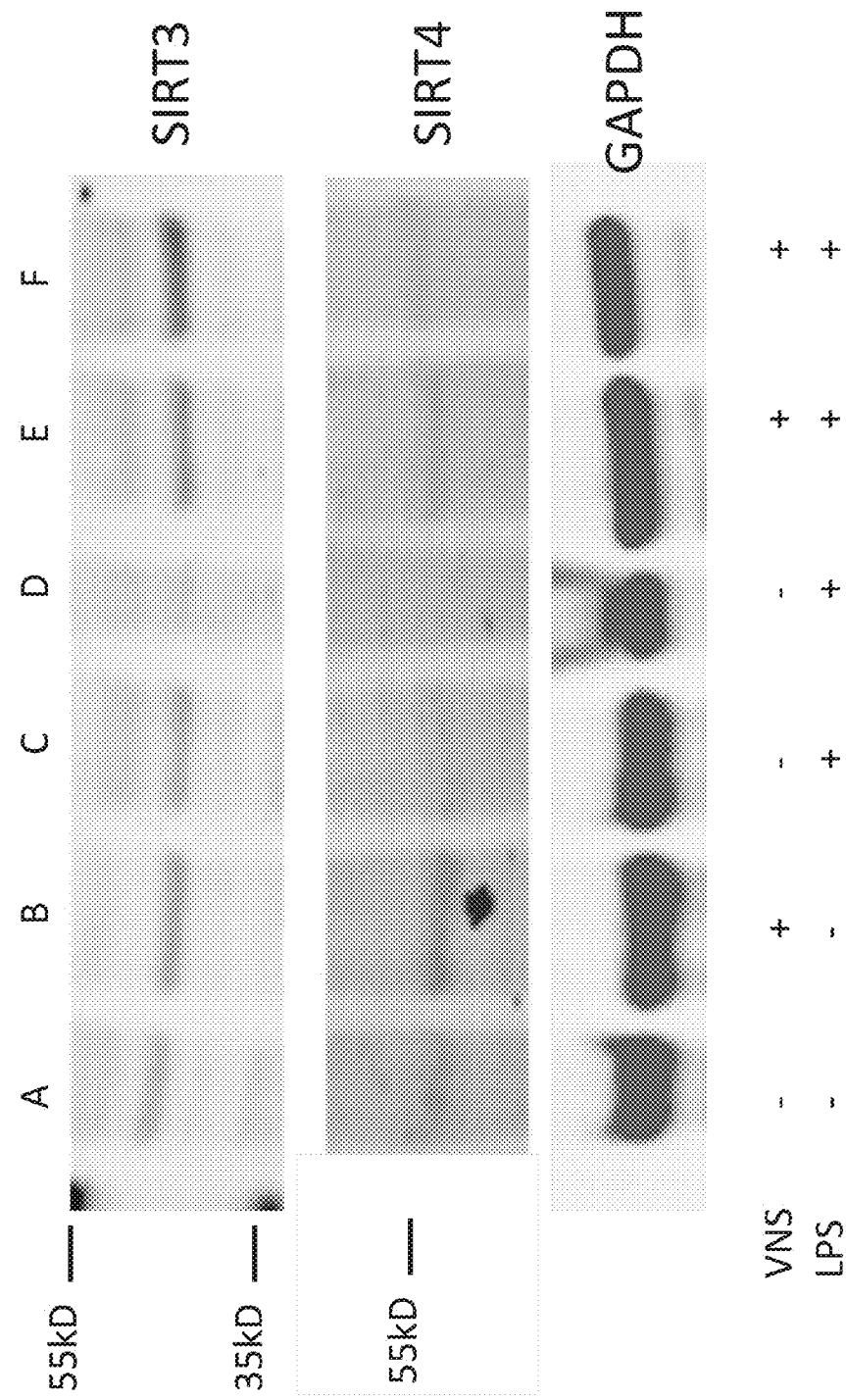
FIG. 6 illustrates VNS up-regulation or maintenance of SIRT3 and SIRT4 in liver in endotoxemia.

FIG. 6 shows that VNS up-regulates SIRT3 and SIRT4 in the liver. For example, lanes A and B show that SIRT3 and SIRT4 are up-regulated in liver in unchallenged mice. Lanes C and D with reference to lane A shows that LPS challenge or endotoxemia in the absence of VNS results in down-regulation of SIRT3 and SIRT4 in the liver (normalized by GADPH signal). Lanes E and F show that VNS up-regulates and/or maintains SIRT3 and SIRT4 levels in liver in endotoxemia.

Figure 7:
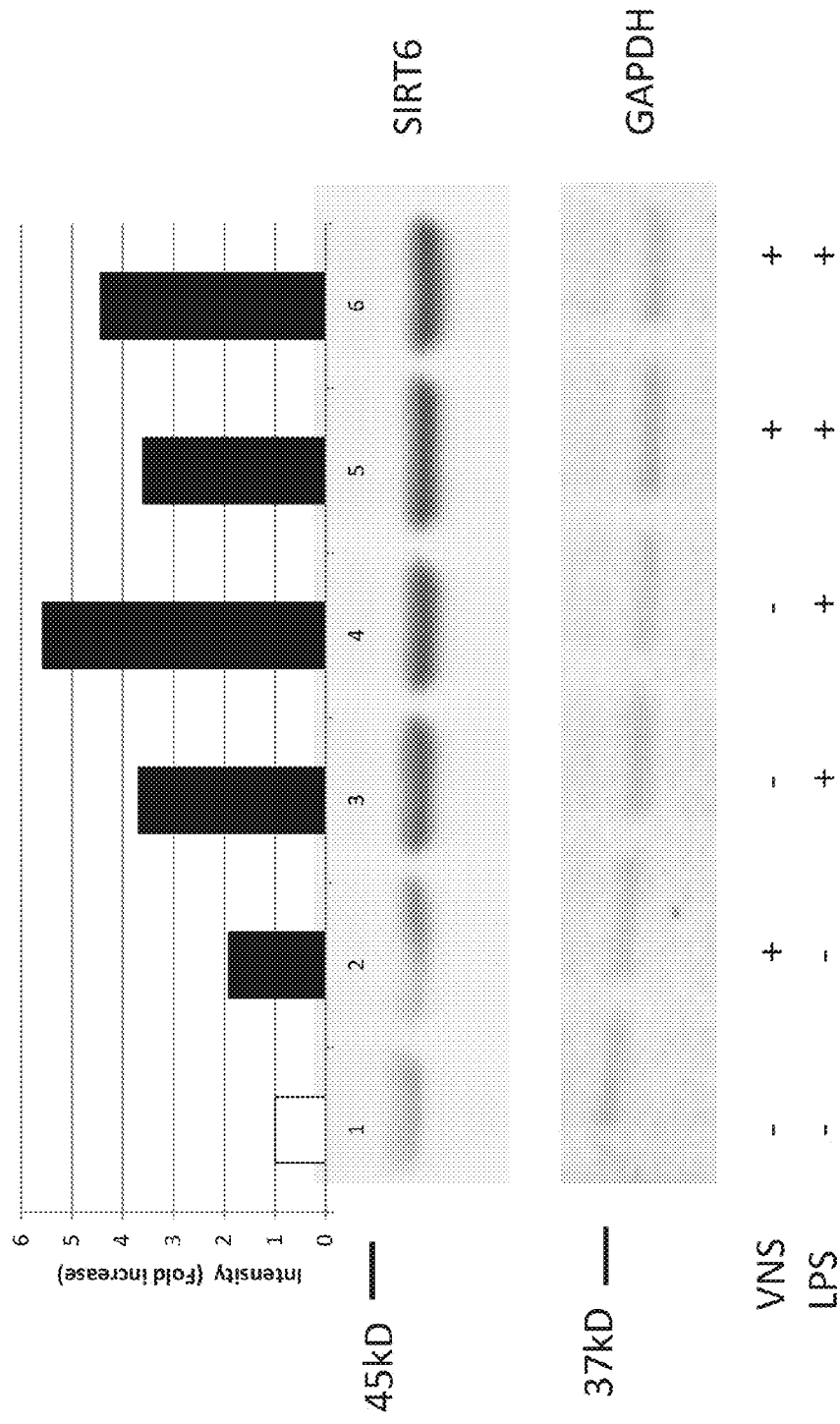
FIG. 7 illustrates VNS up-regulation of SIRT6 in the brain of unchallenged mice.

FIG. 7 shows in lanes 1 and 2 that VNS up-regulates SIRT6 in the brain of unchallenged mice. Intensities are normalized to GAPDH, a marker that corrects for lane to lane total protein variability. This allows the intensities, and thus the concentrations levels, of the SIRT proteins in the different lanes, which are from different mice, to be quantitatively compared to each other. As shown in lanes 1 and 2, VNS stimulation results in about a two fold increase in band intensity for SIRT6 in the brains of unchallenged mice. As shown in lanes 3 and 4, LPS challenge or endotoxemia results in an increase or up-regulation of SIRT6 in the brain, which differs from the results obtained for SIRT1, SIRT3 and SIRT4 in other mice tissues. As shown in lanes 5 and 6, VNS does not appear to have a significant or detectable effect on SIRT6 levels in the brains of challenged mice, which also differs from the results obtained for SIRT1, SIRT3 and SIRT4 in other mice tissues.

Figure 8:
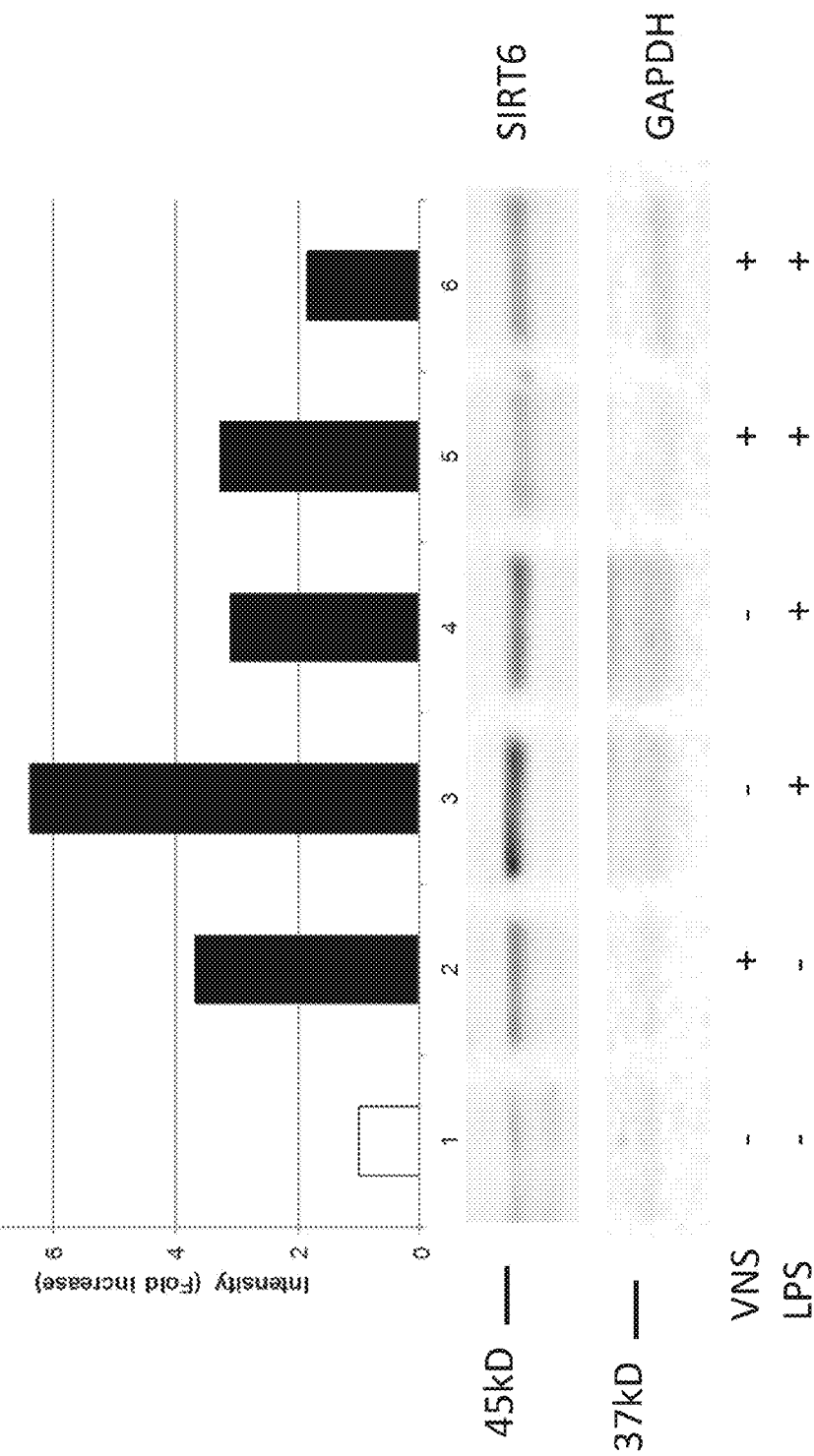
FIG. 8 illustrates VNS up-regulation of SIRT6 in fat of control mice and that VNS dampens the increase in SIRT6 in fat endotoxemia.

FIG. 8 shows in lanes 1 and 2 that VNS up-regulates SIRT6 in the fat of control mice not challenged with LPS. The intensities of the bands are normalized to GAPDH. Lanes 3 and 4 as compared to lane 1 show that LPS challenge increases or up-regulates SIRT6 in fat in endotoxemic or LPS challenged mice. As shown in lanes 5 and 6, VNS dampens the increase or up-regulation of SIRT6 in fat in endotoxemic or LPS challenged mice. Note that the increase in SIRT6 in the fat and brain (see FIG. 7) of endotoxemic mice may be secondary to or offset by the reduction of SIRT1 and SIRT3.

Figure 9A:
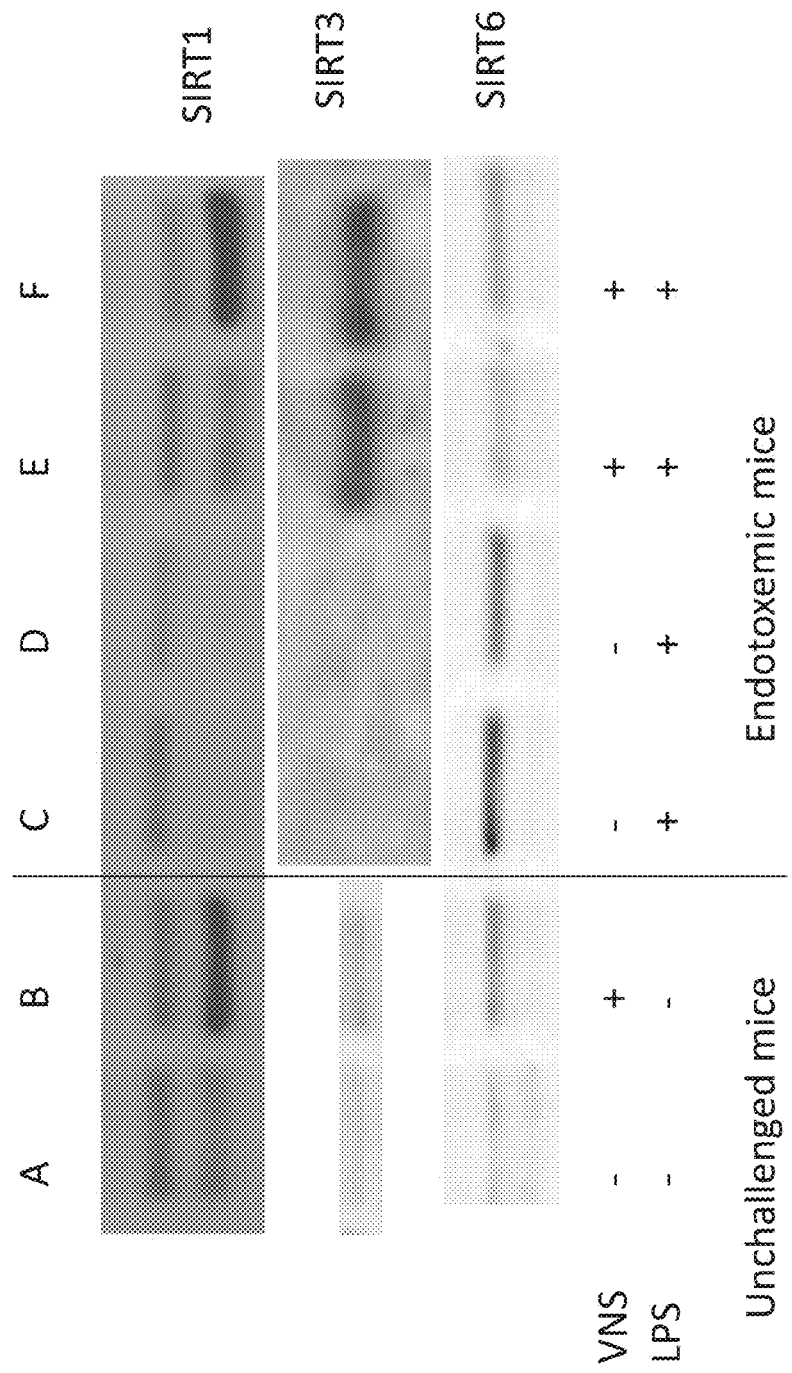
FIG. 9A illustrates the differential regulation of SIRT1, SIRT3 and SIRT6 in white fat following VNS and in the context of endotoxemia.
Figure 9B:
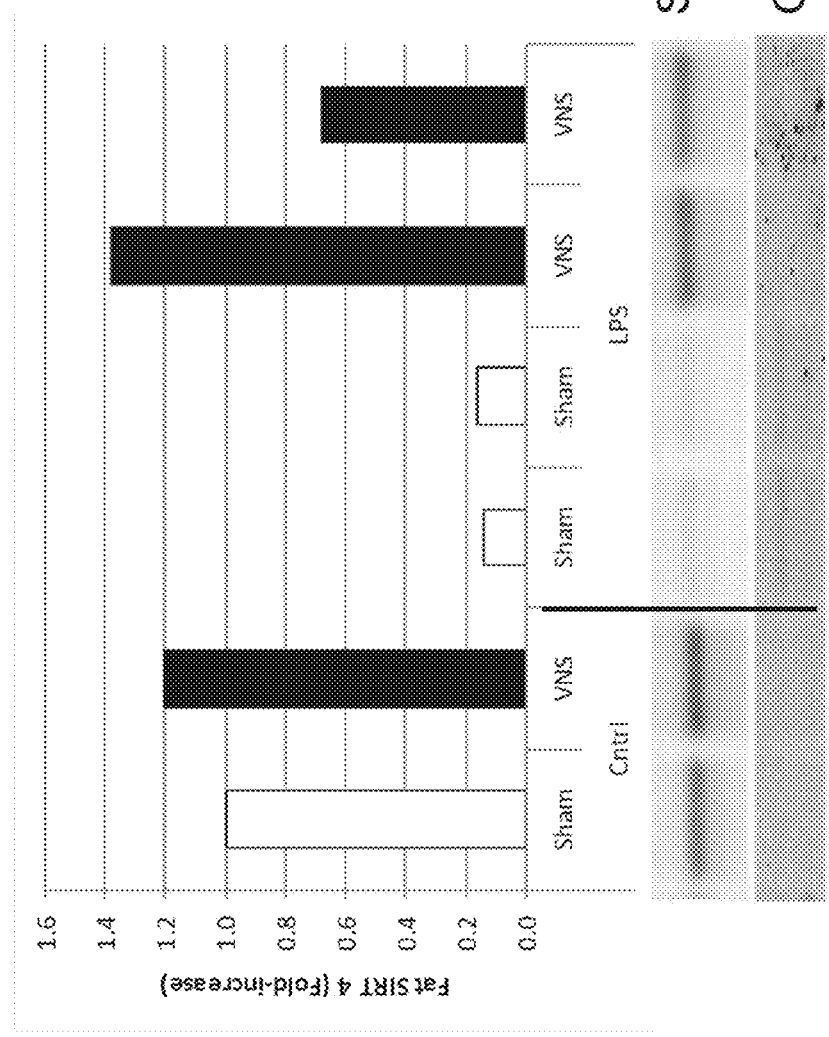
FIG. 9B illustrates VNS up-regulation of SIRT4 in (epididymal) fat and prevention of loss of SIRT4 in an endotoxemia model.

FIG. 9A and FIG. 9B show that SIRTs 1, 3, 6, and 4 in white fat in mice are differentially regulated following VNS and in the context of endotoxemia. As shown in lanes A and B, SIRT1, SIRT3, SIRT6, and SIRT4 all are increased or up-regulated in the fat of unchallenged mice. However, as shown in lanes C and D, SIRT1, SIRT3, and SIRT4 are down-regulated or decreased in the fat of endotoxemic or LPS challenged mice, while SIRT6 is up-regulated or increased in fat of endotoxemic or LPS challenged mice. Also, as shown in lanes E and F, VNS prevents or reduces the decrease of SIRT1, SIRT3, and SIRT4 levels in the fat of endotoxemic or LPS challenged mice, while VNS dampens the increase or up-regulation of SIRT6 in fat of endotoxemic or LPS challenged mice.

FIGS. 10A through 15B illustrate the modulation of SIRT by VNS may depend on the stimulation parameters. In particular, in some variations the amplitude of the applied energy (e.g., current or voltage) delivered may determine which and how much a sirtuin is stimulated. FIGS. 10A through 15B were generated using a protocol modified from that described above for FIGS. 2 through 9. Instead of stimulation at only 1 mA (1000 μA), stimulation using both 500 μA and 1000 μA was performed in order to determine a VNS threshold for activation of sirtuins. In FIGS. 10A to 15B, the detection of tissue protein content was performed by Bradford assay, and western blot detection was done under reducing conditions. Samples were counterstained against GAPDH (goat; Santa Cruz Biotech) using infrared fluorescence detection (LICOR Odyssey). The optical density (OD) of Sirtuins normalized to OD of GAPDH. Animals (rats) were anesthetized, then VNS (e.g., 500 or 1000 μA, 200 μsec pulsewidth, 10 Hz, 60 sec) or sham stimulation (0 μA) was applied using a cuff electrode about the left cervical vagus nerve. In FIGS. 10A, 10B, 11A and 12-15B, mice were allowed to recover for 3 hrs following VNS or sham stimulation, then challenged with LPS or carrier and euthanized 90 minutes post LPS challenge so that tissues may be tested. Thus, the results represent the modulation of sirtuins 4.5 hours after VNS or control for these figures.

The sirtuins may be specifically and separately modulated by appropriate VNS. For example, VNS at various stimulation intensities has been shown to up-regulate TNF in various tissues; the TNF effect of VNS is differently modulated than the VNS modulation of sirtuins. FIGS. 10A and 10B illustrate that TNF is reduced in the spleen following VNS at both 500 μA and 1000 μA. FIGS. 10A and 10B also show that TNF is not reduced in serum following VNS at both 500 μA and 1000 μA. It has been demonstrated that reduction of splenic TN F (pre-released) precedes measurable reduction in serum by about 30 minutes.

Figure 11A:
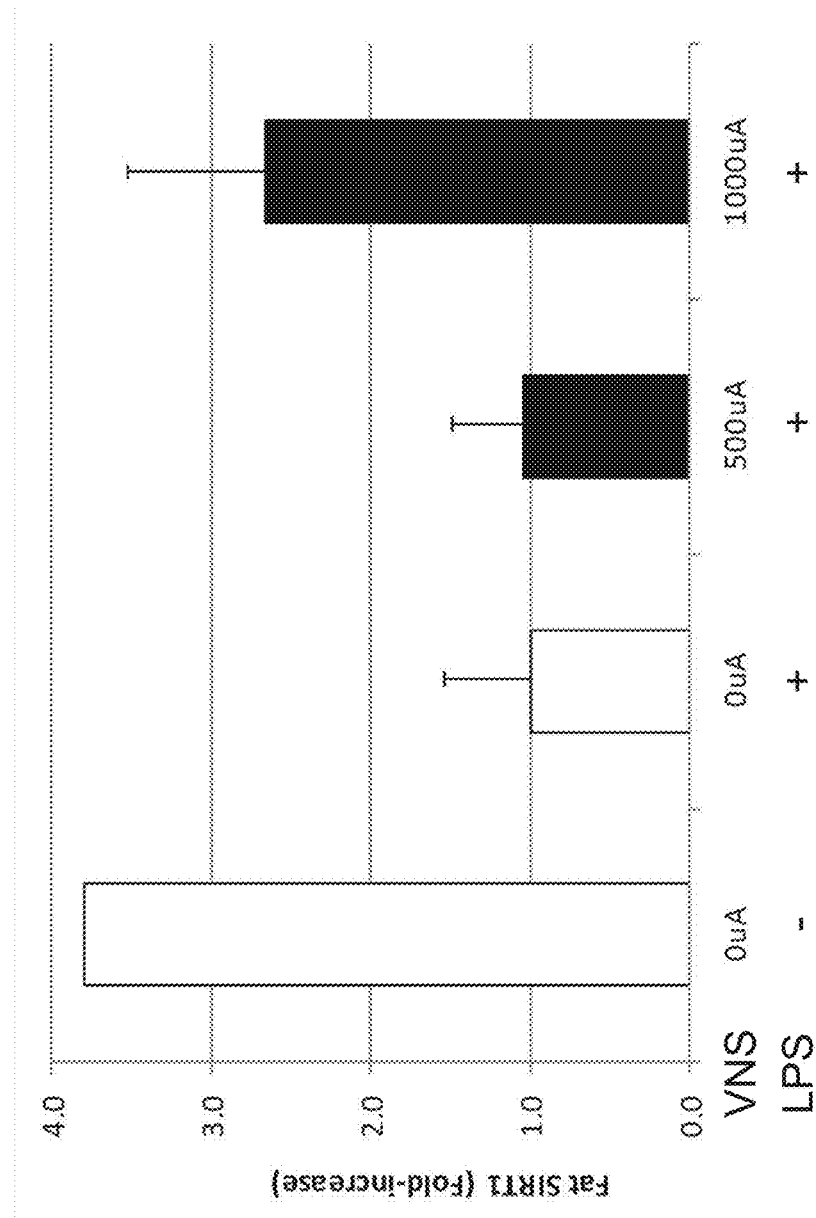
FIG. 11A shows the effect of VNS modulation of SIRT1 in the epididymal (white fat) of a rat using various stimulation parameters.

FIG. 11A shows that VNS at 1000 μA increases or maintain SIRT1 levels in the fat after LPS challenge. However, VNS at 500 μA did not increase or maintain SIRT1 levels in the fat after LPS challenge. Thus, stimulation at 500 μA modulates TNF but does not modulate or activate SIRT1, while stimulation at 1000 μA modulates or activates both TNF and SIRT1. Thus, the threshold for TNF modulation (or modulation of inflammation) is different than the threshold for modulation of at least some of the sirtuins, including SIRT1, in at least some tissues, including fat. VNS may therefore modulate inflammation while not significantly modulating at least some sirtuins, such as SIRT1.

Figure 11B:
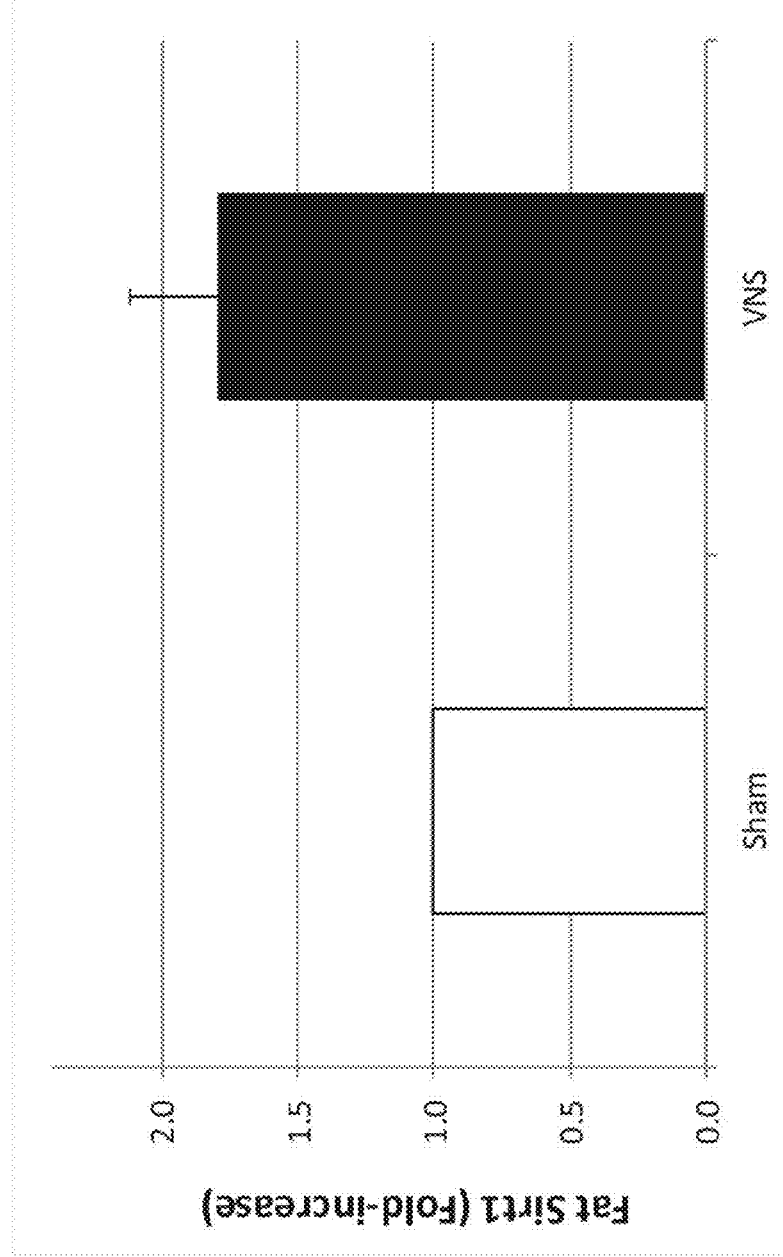
FIG. 11B shows the effect of VNS modulation of SIRT1 after 24 hours post-stimulation.

FIG. 11B shows another set of experiments in which the level of SIRT1 was significantly increased in the epididymal (white fat) of rats that were stimulated with VNS at 1000 μA and allowed to recover for 24 hours. In this example, the effect of VNS on SIRT1 is surprisingly long-lasting; SIRT1 is modulated by VNS for at least 24 h post-stimulation. The stimulation applied is remarkably low duty-cycle over this time period (e.g., a single burst of stimulation over a 24 hour period). In FIG. 11B, VNS (n=3) or sham stimulation (n=2) was applied, and the animals were allowed to recover for 24 hours before tissues were harvested.

Figure 12:
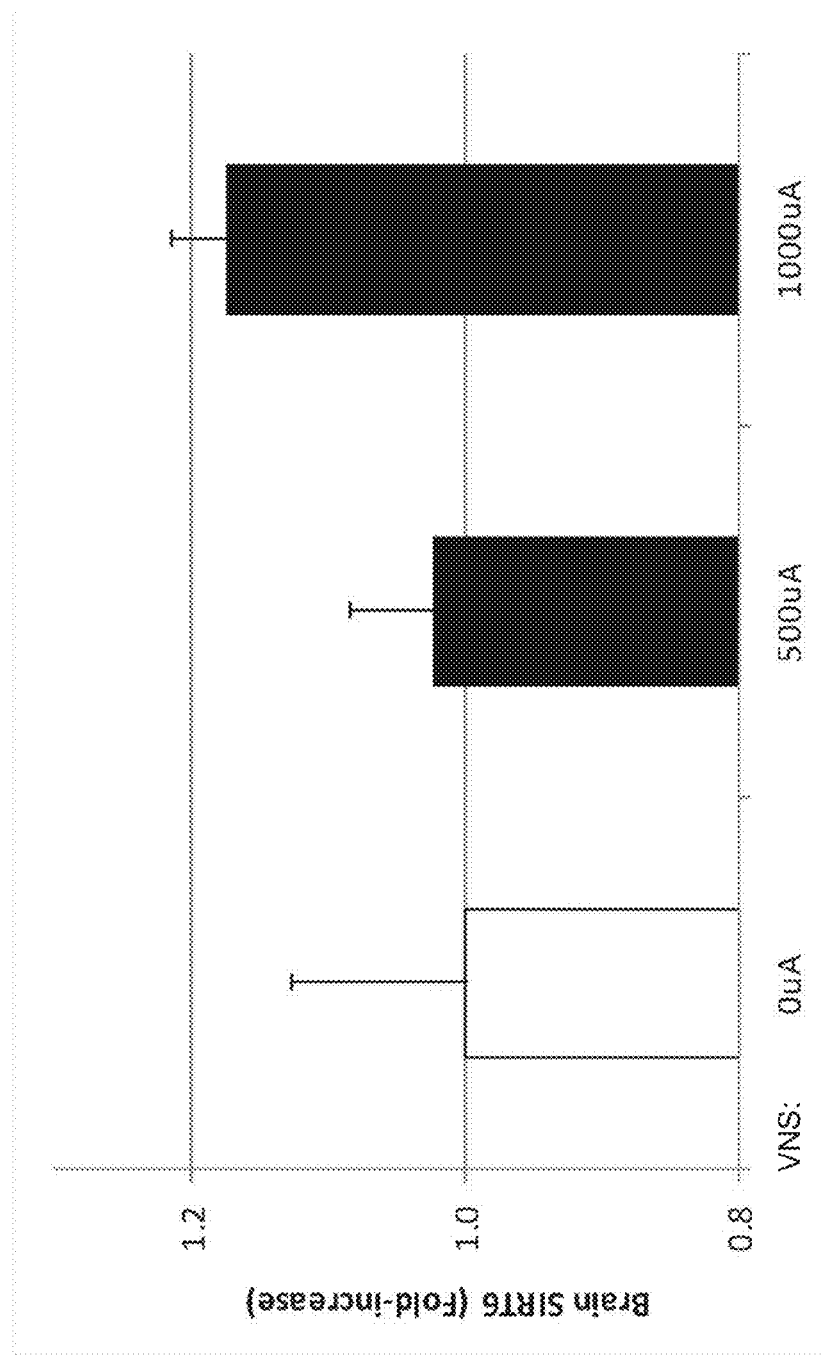
FIG. 12 shows the VNS modulation of SIRT6 in the brain is dependent on the stimulation parameters.

FIG. 12 illustrates that VNS at 1000 μA increases SIRT6 in the brain, while VNS at 500 μA did not increase SIRT6 in the brain.

Figure 13A:
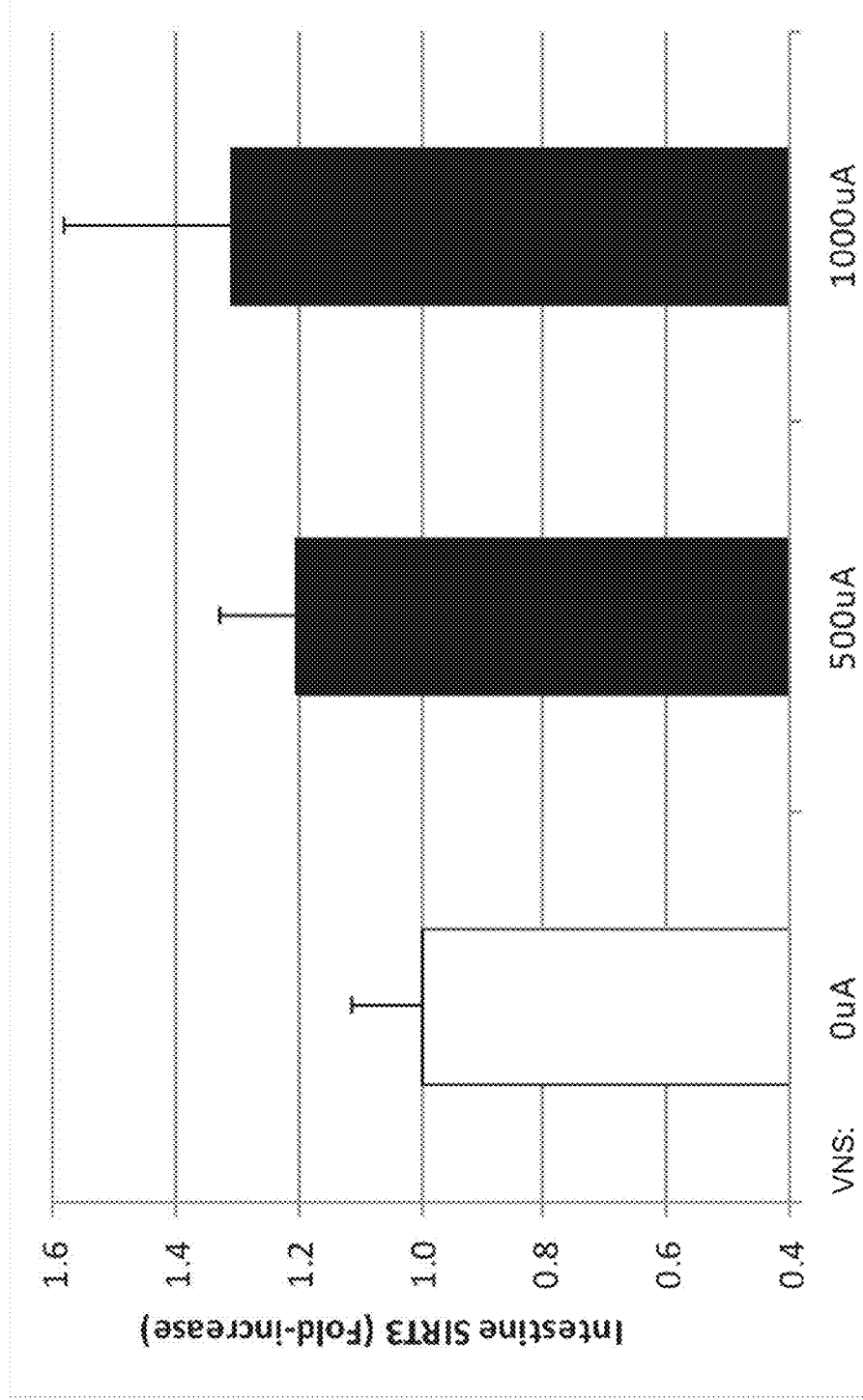
FIG. 13A shows the VNS modulation of SIRT3 in the intestine of the rat is dependent on the stimulation parameters applied.
Figure 13B:
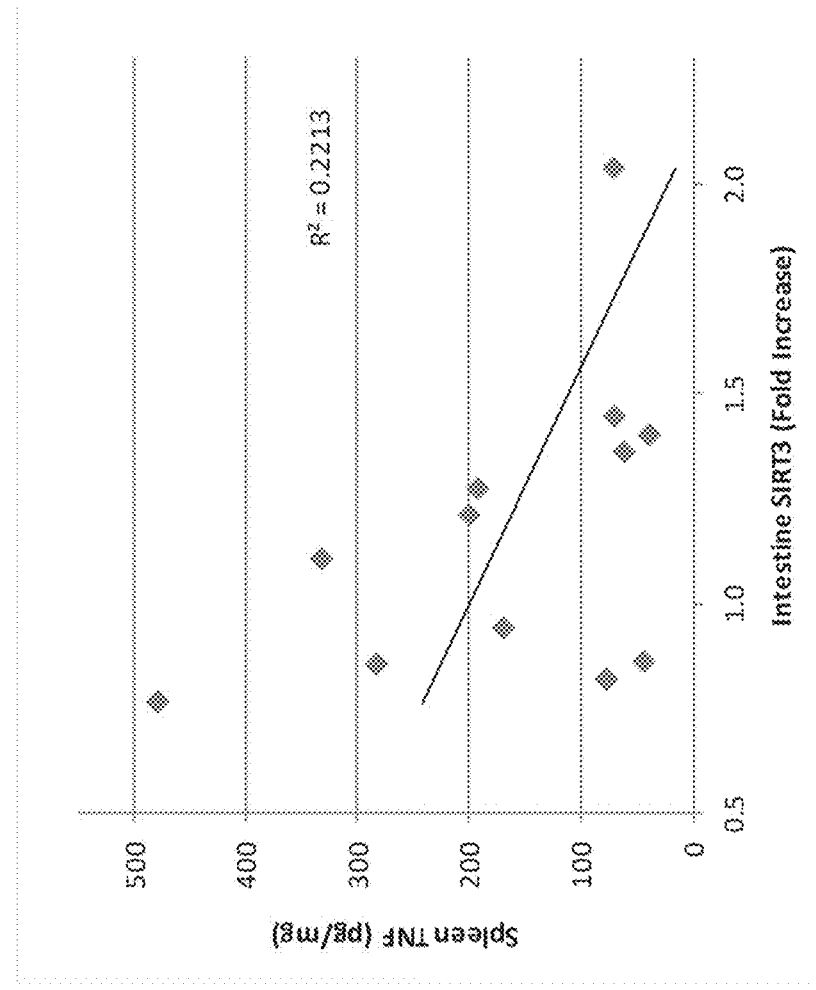
FIG. 13B illustrates an inverse relationship between TNF level in the spleen and SIRT3 level in the intestine.

Interestingly, different sirtuins may be modulated differently based on the VNS stimulation parameters. For example, the threshold for modulation of SIRT3 in the intestine is lower than the VNS threshold for other sirtuins in the body. This is illustrated in FIG. 13A. FIG. 13A illustrates that VNS increases SIRT3 in the intestine at both 500 μA and 1000 μA.

Figure 14:
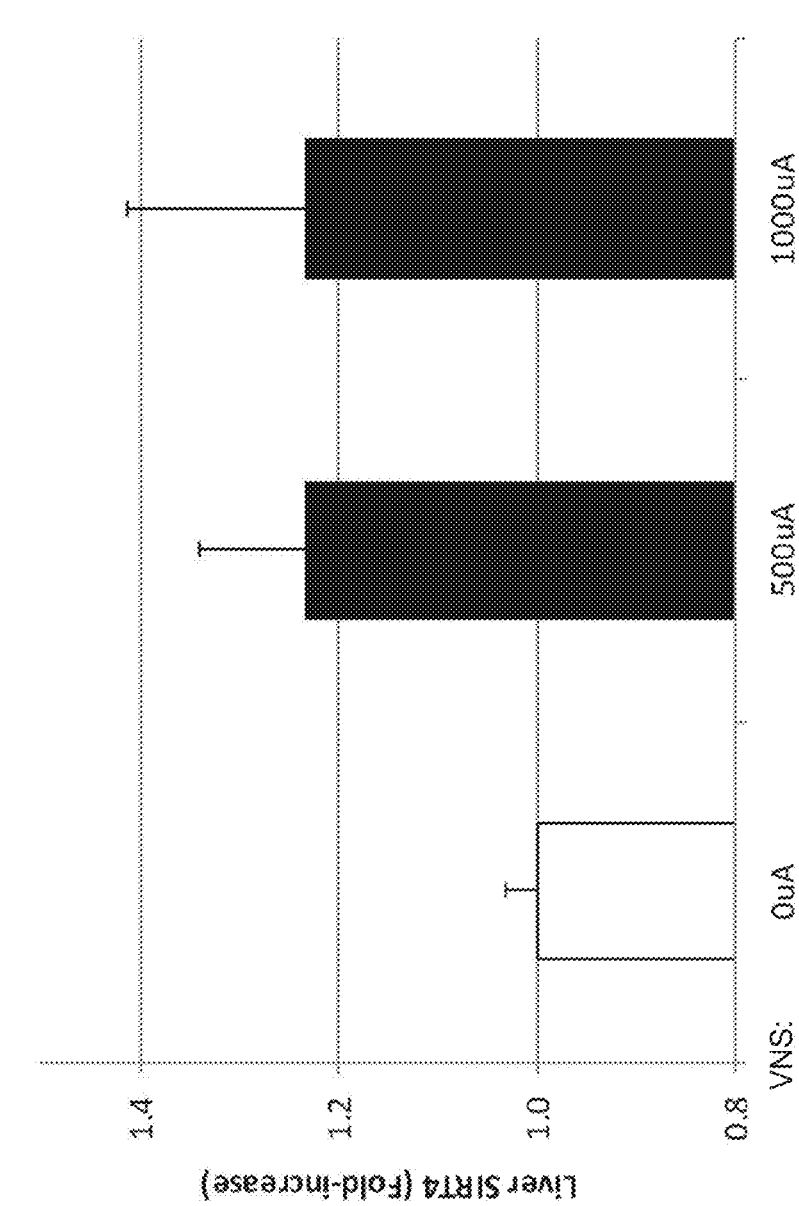
FIG. 14 shows the modulation of SIRT4 in the liver by VNS.
Figure 15A:
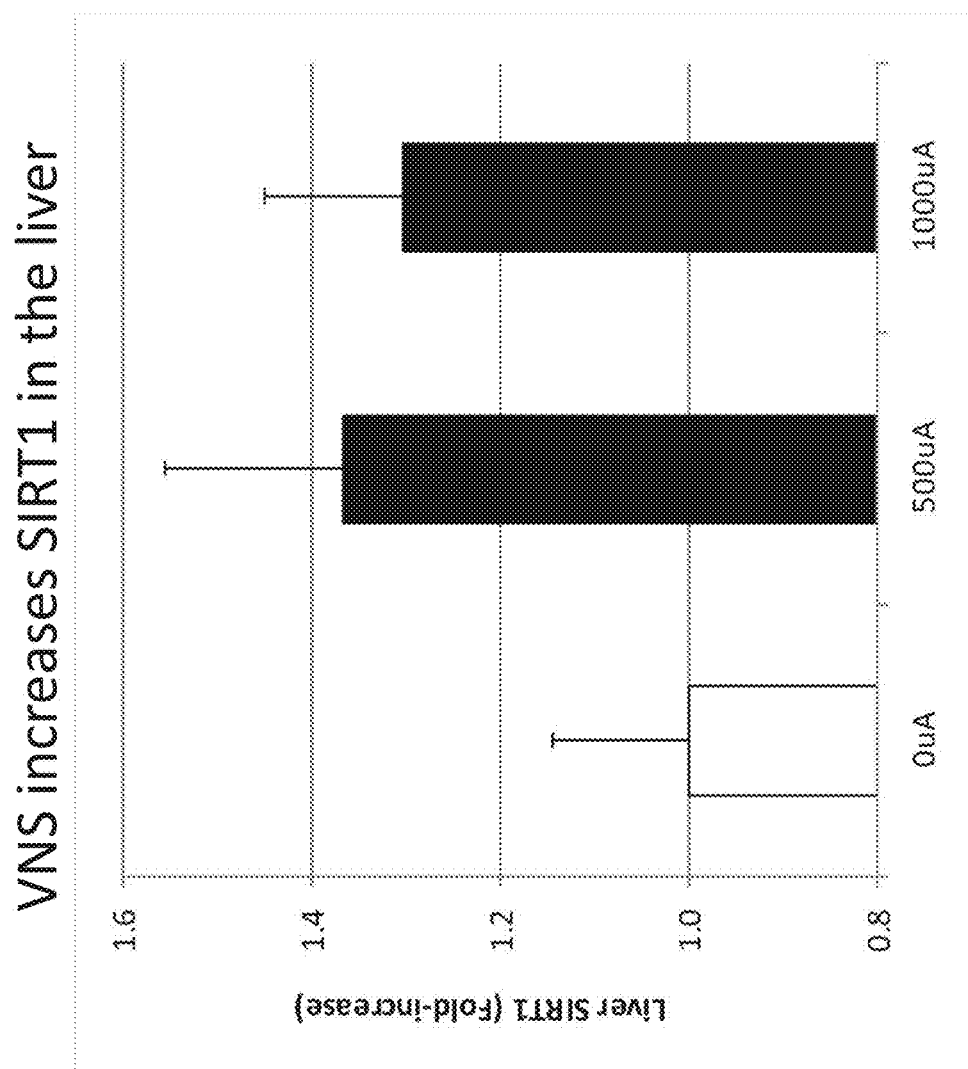
FIG. 15A shows the modulation of SIRT1 in the liver by VNS.
Figure 15B:
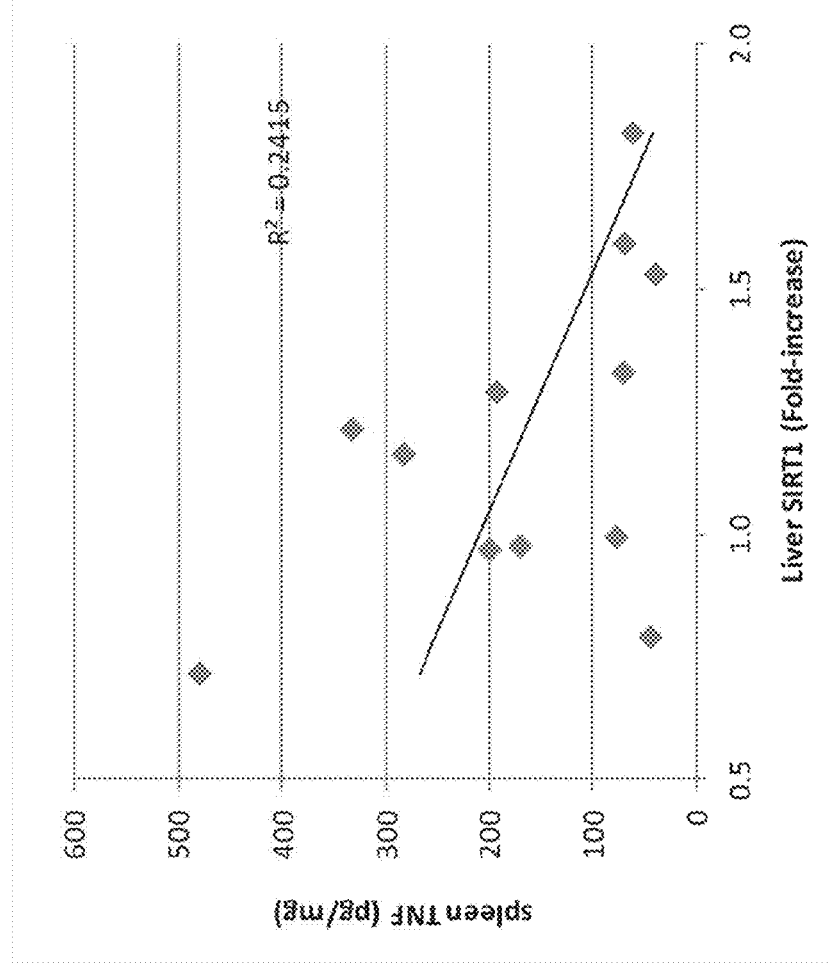
FIG. 15B illustrates an inverse relationship between TNF level in the spleen and SIRT1 level in the liver.

Similarly, SIRT4 and SIRT1 in the liver appears to have a lower threshold for VNS modulation, as shown in FIG. 14 and FIG. 16A. FIG. 14 and FIG. 16A illustrate that VNS increases SIRT4 and SIRT1 in the liver at both 500 μA and 1000 μA. Thus, depending on the parameters (e.g., level) of stimulation applied, different groups of sirtuins can be modulated. For example, at 500 μA SIRT3 in the intestine and SIRT1 and SIRT4 in the liver are both increased, while SIRT 1 in fat and SIRT 6 in the brain are not modulated. At 1000 μA, SIRT1 in fat, SIRT3 in intestine, both SIRT1 and SIRT4 in the liver, and SIRT6 in the brain are all increased. Although the data in FIGS. 10A to 15B originates from relatively small sample size data sets, these preliminary results are both surprising and significant for the specific modulation of SIRTs. It is also potentially significant that the SIRT modulation in the fat were particularly substantial; increases in sirtuins detected elsewhere were far more modest using the parameters described above (e.g., 1.2-1.5 fold increases over sham).

In some variations SIRT modulation may be achieved using stimulation parameters similar to those of NCAP; in some variations, the VNS parameters for modulation of sirtuins may be different. Without being bound by theory, we herein hypothesize that SIRT modulation may be dependent on the same cholinergic pathways as the vagus nerve stimulation modulation of endotoxemia and other inflammatory diseases. Alternatively, modulation of SIRTs by VNS may be occurring through independent vagal pathways that do not overlap with the CAP and are not dependent on the acetylcholine receptor. In some embodiments, differential levels of various sirtuins are monitored during treatment. The levels of one or more sirtuins can be used, for example, as a biomarker for another biomolecule or state or condition of a patient. For example, in some embodiments, the level of one or more sirtuins may generally be inversely correlated with levels of TNF such that increasing or increased levels of a particular sirtuin may indicate decreasing or decreased levels of TNF.

Another pathway that can be modulated via SIRT modulation includes the heat shock response (HSR) which is mediated through heat shock factor 1 (HSF1). HSF1 has been shown to protect cells from damage associated with mis-folded proteins and has also been shown to regulate the insulin-signaling pathway and aging. For example, activation and/or up-regulation of at least one member of the SIRT family, such as SIRT1, promotes deacetylation of HSF1, which enhances HSF1 binding to the heat shock promoter Hsp70 on DNA, which is associated with aging. Reduced HSF1 activity has been shown to accelerate tissue aging and shorten lifespan in *C. elegans*. See U.S. Publication No. 2009/0276019 to Perez et al.; Westerheide et al., Stress-inducible regulation of heat shock factor 1 by the deacetylase SIRT1, *Science*, 2009 Feb. 20; 323(5917):1063-6, both of which are herein incorporated by reference in their entireties.

Another pathway that can be modulated via SIRT modulation includes the forkhead box transcription factors, particularly the class O members of the forkhead box class of proteins. See U.S. Publication No. 2009/0276019 to Perez et al.; van der Horst et al., Stressing the role of FoxO proteins in lifespan and disease, Nat. Rev. Mol. Cell. Biol., 2007 June; 8(6):440-50, both of which are herein incorporated by reference in their entireties. Members of the class O forkhead box proteins (FoxO), such as DAF-16 which functions along the insulin/IGF-1 signaling pathway, are important in metabolism, cellular proliferation, stress tolerance and lifespan. The activity of FoxO proteins are regulated by post-translational modifications, including phosphorylation, acetylation and ubiquitylation. Members of the sirtuins, such as SIRT1, have been shown to deacetylate FoxO transcription factors, such as DAF-16, that contribute to cellular regulation, including stress and longevity. Up-regulation and/or increased activity of sirtuins, such as SIRT1 and SIRT2 which are also up-regulated during dietary restriction and caloric intake interventions, lead to deacetylation and enhanced transcriptional activation of DAF-16/FoxO, which has been linked with increased longevity.

The invention may be embodied in other specific forms without departing from the essential attributes thereof; therefore, the illustrated embodiments should be considered in all respects as illustrative and not restrictive. The claims provided herein are to ensure adequacy of the present application for establishing foreign priority and for no other purpose.

What is claimed is:

1. A method of modulating sirtuin (SIRT) activity and/or level in a patient, the method comprising measuring a level of SIRT in the patient; identifying that the patient is in need of SIRT modulation based at least in part on the measured level of SIRT; and modulating SIRT activity and/or level by applying stimulation to the patient's vagus nerve from an implanted micro stimulator.

2. The method of claim 1, wherein applying comprises applying stimulation from the microstimulator to the vagus nerve to modulate SIRT activity and/or level to treat cancer, to enhance longevity, to treat a metabolic syndrome, to treat or prevent liver cirrhosis/fatty liver, to treat or prevent muscle disorders such as Sarcopenia or disuse atrophy, to treat a circadian rhythm disorder, to treat insomnia, and/or to treat a CNS disorder including Alzheimer's, Parkinson's, or Huntington's diseases.

3. The method of claim 1, further comprising applying stimulation in conjunction with one or more SIRT modulating active agents selected from the group consisting of: drugs, medical food, probiotics.

4. The method of claim 1, wherein applying stimulation comprises applying electrical VNS having an amplitude of greater than 1000 μA.

5. The method of claim 1, wherein applying stimulation comprises applying electrical VNS having an amplitude of between 150 μA and 5 mA, a pulse width of between 50 μsec and 1 msec, a frequency of between 1 Hz and 100 Hz, a duration of between 1 sec and 5 min, an interpulse interval of between 10 μsec and 950 μsec.

6. The method of claim 1, wherein applying stimulation comprises applying electrical stimulation sufficient to modulate only a sub-set of SIRTs without modulating another sub-set of SIRTs.

7. The method of claim 1, wherein applying stimulation comprises applying repeated electrical stimulation separated by an off-time of greater than 8 hours.

8. The method of claim 1, wherein applying comprises applying extremely low duty cycle electrical energy.

9. The method of claim 1, wherein applying comprises applying stimulation from the microstimulator to the vagus nerve to modify the patient's circadian cycles by modulating SIRT activity and/or level.

10. A method of treating a disorder by modulating sirtuin (SIRT activity and/or level in a patient, the method comprising measuring a level of SIRT in the patient; identifying that the patient is in need of SIRT modulation based at least in part on the measured level of SIRT; and modulating SIRT activity and/or level by applying stimulation from a stimulator to stimulate the vagus nerve.

11. The method of claim 10, further comprising modifying the stimulation based on feedback from one or more biomarker.

12. The method of claim 11, wherein modifying the stimulation comprises modifying one or more of the time, duration, frequency, intensity, and/or interval of an electrical stimulation.

13. The method of claim 10, further comprising applying stimulation in conjunction with one or more SIRT modulating active agents selected from the group consisting of: drugs, medical food, probiotics.

14. The method of claim 10, wherein applying stimulation comprises applying electrical VNS having an amplitude of greater than 1000 µA.

15. The method of claim 10, wherein applying stimulation comprises applying electrical VNS having an amplitude of between 150 µA and 5 mA, a pulse width of between 50 µsec and 1 msec, a frequency of between 1 Hz and 100 Hz, a duration of between 1 sec and 5 min, an interpulse interval of between 10 µsec and 950 µsec.

16. The method of claim 10, wherein applying stimulation comprises applying electrical stimulation sufficient to modulate only a sub-set of SIRTs without modulating another sub-set of SIRTs.

17. The method of claim 10, wherein applying stimulation comprises applying repeated electrical stimulation separated by an off-time of greater than about 8 hours.

18. The method of claim 10, wherein applying comprises applying extremely low duty cycle electrical energy.

19. The method of claim 10, wherein applying comprises applying stimulation from an implanted microstimulator to the vagus nerve.

20. The method of claim 10, further comprising coordinating the application of stimulation from the stimulator based on the patient's circadian rhythm.

21. The method of claim 20, wherein coordinating comprises synchronization or asynchronization of stimulation with circadian rhythm to modulate disease.

22. The method of claim 10, wherein modulating SIRT activity and/or level includes modifying the activity and/or level of a plurality of different sirtuins.

23. The method of claim 22, wherein the plurality of different sirtuins includes SIRT1, SIRT3, SIRT4 and SIRT6.

24. The method of claim 10, wherein modulating SIRT activity and/or level includes increasing the activity and/or level of a first sirtuin and decreasing the activity and/or level of a second sirtuin.

* * * * *